(12) United States Patent
Gillis

(10) Patent No.: US 11,266,877 B2
(45) Date of Patent: Mar. 8, 2022

(54) REHABILITATION SYSTEM AND METHOD THEREFOR

(71) Applicant: Matthew Gillis, River Ryan (CA)

(72) Inventor: Matthew Gillis, River Ryan (CA)

(*) Notice: Subject to any disclaimer, the term of this patent is extended or adjusted under 35 U.S.C. 154(b) by 3 days.

(21) Appl. No.: 16/545,436

(22) Filed: Aug. 20, 2019

(65) Prior Publication Data
US 2020/0061414 A1  Feb. 27, 2020

Related U.S. Application Data

(60) Provisional application No. 62/720,240, filed on Aug. 21, 2018.

(51) Int. Cl.
*A63B 24/00* (2006.01)
*A63B 21/00* (2006.01)
*A61H 1/02* (2006.01)
*A63B 21/02* (2006.01)
(Continued)

(52) U.S. Cl.
CPC ......... *A63B 24/0006* (2013.01); *A61H 1/024* (2013.01); *A63B 21/00069* (2013.01); *A63B 21/028* (2013.01); *G16H 20/30* (2018.01); *G16H 20/40* (2018.01); *A61H 2230/605* (2013.01); *A63B 2024/0015* (2013.01)

(58) Field of Classification Search
CPC .......... A63B 24/0006; A63B 21/00069; A63B 21/028; A63B 2024/0015; G16H 20/40; G16H 20/30; A61H 1/024; A61H 2230/605
See application file for complete search history.

(56) References Cited

U.S. PATENT DOCUMENTS

| 2,115,926 A | 5/1938 | Hatton |
| 4,023,808 A | 5/1977 | Hebert |
| 4,852,874 A | 8/1989 | Sleichter et al. |

(Continued)

FOREIGN PATENT DOCUMENTS

KR  20180019258 A  8/2018

OTHER PUBLICATIONS

Togu, "Pressure Air Biofeedback", FEI Fabrication Enterprises Inc., available at: https://www.fab-ent.com/exercise/togu/pressure-air-biofeedback.

(Continued)

*Primary Examiner* — Mohamed Charioui
*Assistant Examiner* — Christine Y Liao
(74) *Attorney, Agent, or Firm* — Bereskin & Parr LLP

(57) ABSTRACT

A knee rehabilitation system includes a plurality of compressible resistance members, a knee garment, and a resistance member receptacle. Each compressible resistance member in the plurality of compressible resistance members has (i) a same size and a shape as each other compressible resistance member in the plurality of compressible resistance members, and (ii) a compression resistance different from each other compressible resistance member in the plurality of compressible resistance members. The knee garment has a knee garment ventral portion and a knee garment dorsal portion. The resistance member receptacle is coupled to the knee garment dorsal portion, and the resistance member receptacle is sized to carry each compressible resistance member in the plurality of compressible resistance members, one at a time.

17 Claims, 29 Drawing Sheets

(51) Int. Cl.
*G16H 20/40* (2018.01)
*G16H 20/30* (2018.01)

(56) References Cited

U.S. PATENT DOCUMENTS

| | | | |
|---|---|---|---|
| 5,131,408 | A | 7/1992 | Smith |
| 5,338,276 | A | 8/1994 | Jull et al. |
| 5,556,374 | A | 9/1996 | Grace et al. |
| 5,626,537 | A | 5/1997 | Danyo et al. |
| 6,358,187 | B1 * | 3/2002 | Smith ............... A63B 21/002 482/4 |
| 6,547,703 | B1 | 4/2003 | Swezey et al. |
| 6,551,264 | B1 | 4/2003 | Cawley et al. |
| 7,182,717 | B2 | 2/2007 | Tanglos |
| 9,033,855 | B2 | 5/2015 | Opfer |
| 9,616,272 | B1 | 4/2017 | Bennett |
| 2006/0217248 | A1 | 9/2006 | Diseati |
| 2008/0146336 | A1 * | 6/2008 | Feldman ............... A63F 13/24 463/37 |
| 2012/0035020 | A1 | 2/2012 | Kamm |
| 2012/0184418 | A1 | 7/2012 | Wilson |
| 2013/0345603 | A1 | 12/2013 | Pienaar |
| 2014/0194250 | A1 * | 7/2014 | Reich ............... A63B 24/0062 482/5 |
| 2018/0015284 | A1 * | 1/2018 | Coleman ............... A61N 1/0452 |
| 2019/0126097 | A1 * | 5/2019 | Thomson ............ A63B 21/0557 |

OTHER PUBLICATIONS

"Hyfit" Product page, Hifit, Inc., 2020, available at: https://www.hyfitgear.com.
"Circuband" Product Page, Circuband Limited, 2020, Christchurch, New Zealand, available at: https://www.circuband.com.
"Kiio" Product Page, Kiio Inc., 2020, Madison, Wisconsin, United States, available at: https://kiio.com.
Move It—North America, "Move It" Product Page, Eggplant Technologies Ltd., 2018, Hong Kong, available at: http://move-it.club/en/index.html.
"PlayBall Smart Therapy Ball" Product Page, Playwork, 2019, Israel, available at: https://www.playwork.me.

* cited by examiner

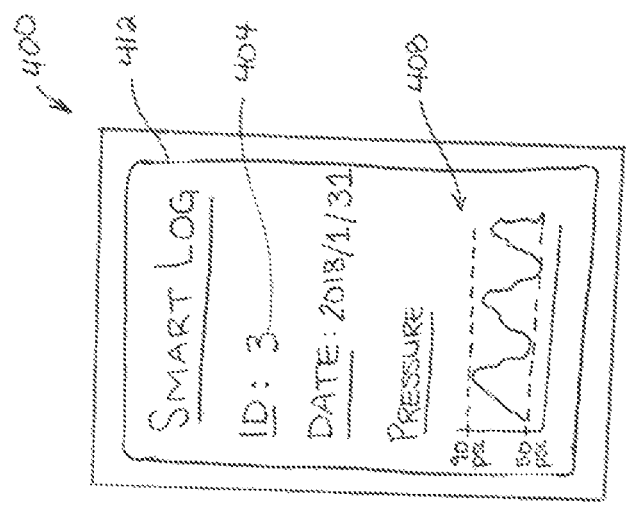
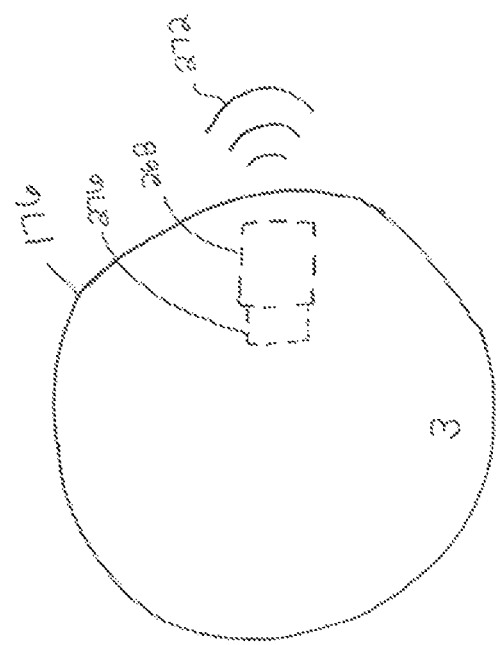
FIG. 14

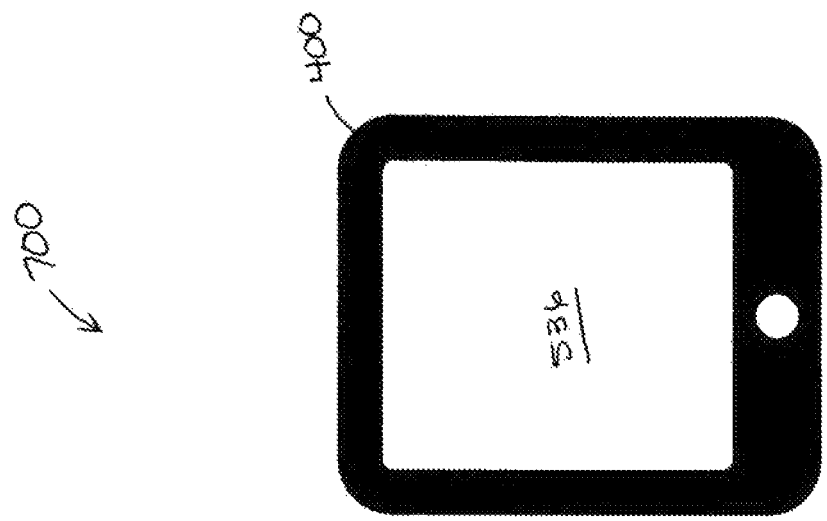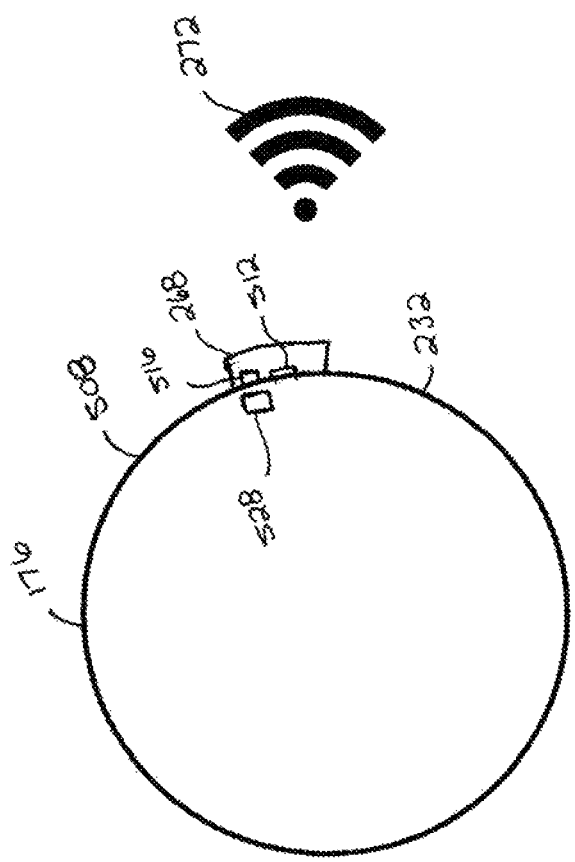
FIG. 16

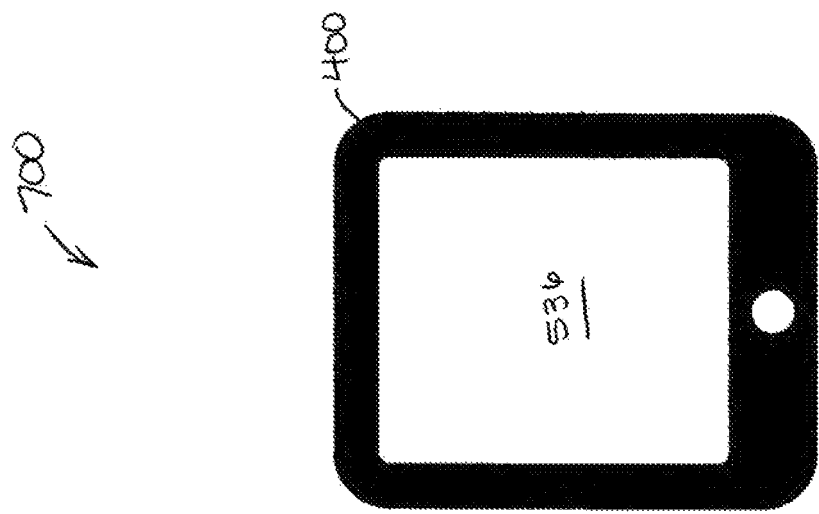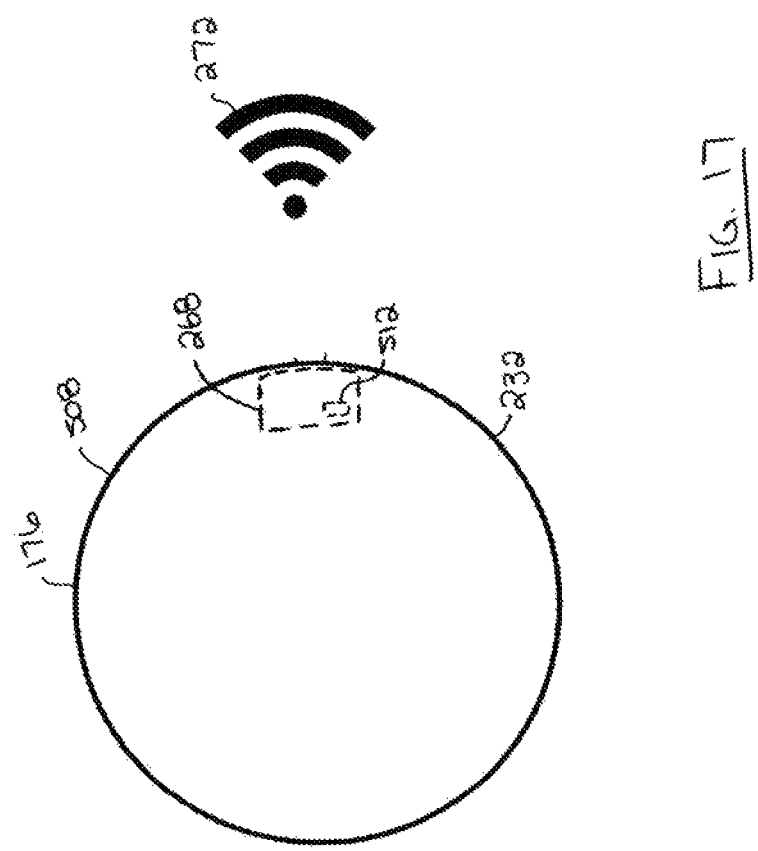
FIG. 17

REHABILITATION SYSTEM AND METHOD THEREFOR

FIELD

The field of this disclosure relates to knee rehabilitation systems and methods therefor.

INTRODUCTION

Patellofemoral pain syndrome (PFPS) is among the most common knee impairments. A common source of PFPS is weakness of the VMO (vastus medialis obliquus) muscle, which in turn can result in improper alignment of the patella (kneecap). Exercises which target the knee and VMO muscles are commonly used to rehabilitate PFPS as well as various other knee impairments.

SUMMARY

In one aspect, a knee rehabilitation system is provided. The knee rehabilitation system includes a plurality of compressible resistance members, a knee garment, and a resistance member receptacle. Each compressible resistance member in the plurality of compressible resistance members has (i) a same size and shape as each other compressible resistance member in the plurality of compressible resistance members, and (ii) a compression resistance different from each other compressible resistance member in the plurality of compressible resistance members. The knee garment has a knee garment ventral portion and a knee garment dorsal portion. The resistance member receptacle is coupled to the knee garment dorsal portion, the resistance member receptacle sized to carry each compressible resistance member in the plurality of compressible resistance members, one at a time.

In another aspect, a knee compression garment is provided. The garment includes a resiliently stretchable body, and a compressible resistance member mount. The resiliently stretchable body includes a first leg portion having a distal opening, a second leg portion having a proximal opening, and a knee portion connecting the first leg portion to the second leg portion, wherein the knee portion has a knee ventral portion and a knee dorsal portion. The compressible resistance member mount is connected to the knee dorsal portion and extends dorsally of the knee dorsal portion.

In another aspect, an rehabilitation system is provided. The rehabilitation system includes a resistance sensor, a memory, and one or more processors. The resistance sensor connectable to an exercise device. The memory storing computer readable instructions and a lower threshold resistance percentage. The one or more processors collectively communicatively coupled to the resistance sensor and the memory, and configured to execute the computer-readable instructions. The computer readable instructions when executed configuring the one or more processors to (i) collectively receive sensory data from the resistance sensor indicative of a one repetition maximum resistance measured by the resistance sensor, and after (i), one or many iterations of receive, from the resistance sensor, sensory data indicative of a resistance measured by the resistance sensor, and in response to determining that the resistance exceeds the lower threshold resistance percentage of the one repetition maximum resistance, either register a successful repetition or start an isometric-interval timer.

In another aspect, a rehabilitation method is provided. The rehabilitation method may include
(i) receiving, by one or more processors collectively, from a resistance sensor connected to an exercise device, sensory data indicative of a one repetition maximum resistance measured by the resistance sensor; and
after (i), one or more iterations of:
a) receiving, from the resistance sensor, sensory data indicative of a resistance measured by the resistance sensor, and
b) in response to determining that the resistance exceeds a lower threshold resistance percentage of the one repetition maximum resistance, either registering a successful repetition or starting an isometric-interval timer.

DRAWINGS

FIG. 14 shows a compressible resistance member having a transmitter and an electronic device receiving transmissions from the transmitter, in accordance with an embodiment;

FIG. 16 is a schematic illustration of a rehabilitation system in accordance with an embodiment;

FIG. 17 is a schematic illustration of a rehabilitation system in accordance with an embodiment;

DESCRIPTION OF VARIOUS EMBODIMENTS

Figure 1:
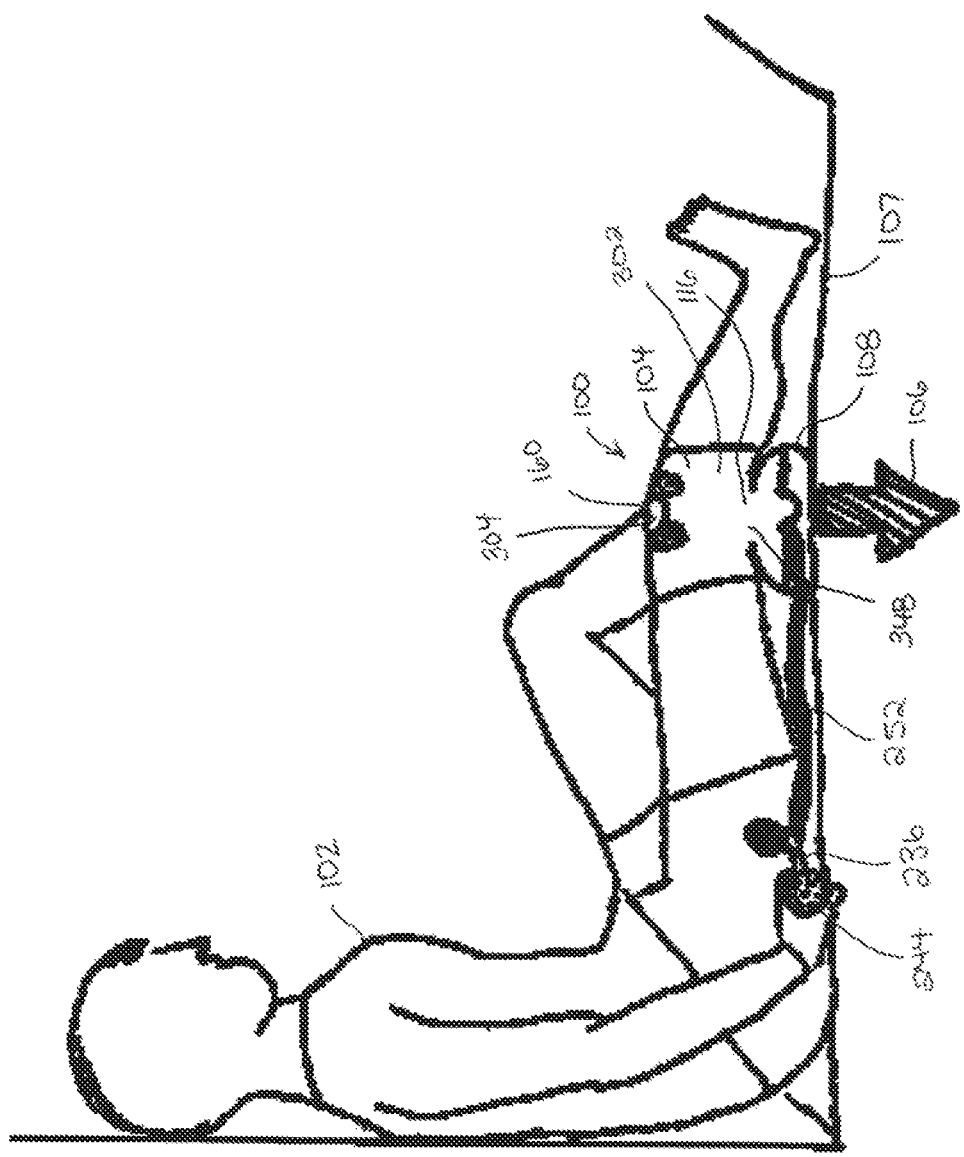
FIG. 1 shows a user wearing a knee rehabilitation system and performing a closed kinetic chain rehabilitation exercise.

Numerous embodiments are described in this application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with modification and alteration without departing from the teachings disclosed herein. Although particular features of the present invention may be described with reference to one or more particular embodiments or figures, it should be understood that such features are not limited to usage in the one or more particular embodiments or figures with reference to which they are described.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", "joined", "affixed", or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", "directly affixed", or "directly fastened" where the parts are connected in physical contact with each other. As used herein, two or more parts are said to be "rigidly coupled", "rigidly connected", "rigidly attached", "rigidly joined", "rigidly affixed", or "rigidly fastened" where the parts are coupled so as to move as one while maintaining a constant orientation relative to each other. None of the terms "coupled", "connected", "attached", "joined", "affixed", and "fastened" distinguish the manner in which two or more parts are joined together.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

As used herein and in the claims, a group of elements are said to 'collectively' perform an act where that act is performed by any one of the elements in the group, or performed cooperatively by two or more (or all) elements in the group.

As used herein and in the claims, a first element is said to be "received" in a second element where at least a portion of the first element is received in the second element unless specifically stated otherwise.

Some elements herein may be identified by a part number, which is composed of a base number followed by an alphabetical or subscript-numerical suffix (e.g. 112a, or $112_1$). Multiple elements herein may be identified by part numbers that share a base number in common and that differ by their suffixes (e.g. $112_1$, $112_2$, and $112_3$). All elements with a common base number may be referred to collectively or generically using the base number without a suffix (e.g. 112).

Exercises targeting the knee and VMO muscles are commonly used to rehabilitate PFPS as well as various other knee impairments. Referring to FIG. 1, embodiments herein relate to a knee rehabilitation system 100 that may be equipped (e.g. worn) by a user 102 around their knee region and used to perform various knee rehabilitation exercises. Knee rehabilitation system 100 may be used to perform exercises targeting the user's knee and VMO muscles (which may be referred to as "VMO exercises"). For example, knee rehabilitation system 100 may be used to perform isometric and/or isotonic exercises, in accordance with open and/or closed kinetic chain methods.

Figure 2B:
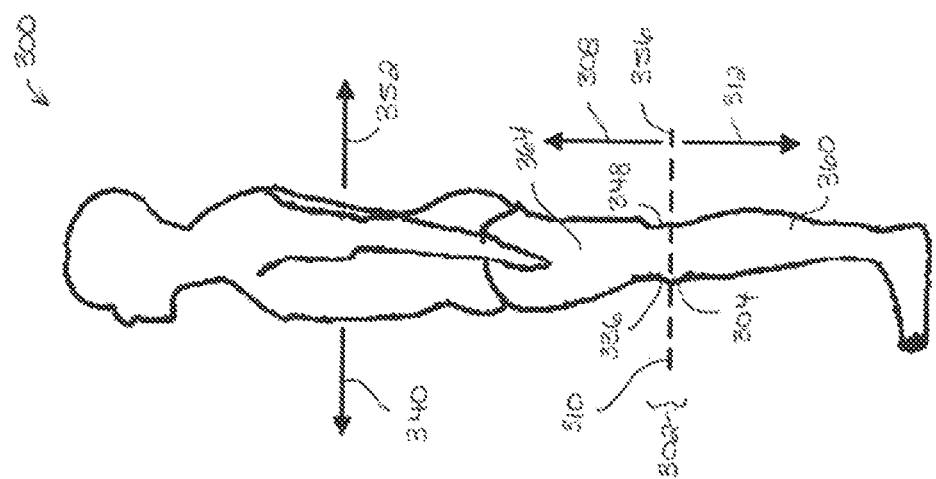
FIG. 2B shows a side schematic representation of the human body of FIG. 2A.
Figure 2A:
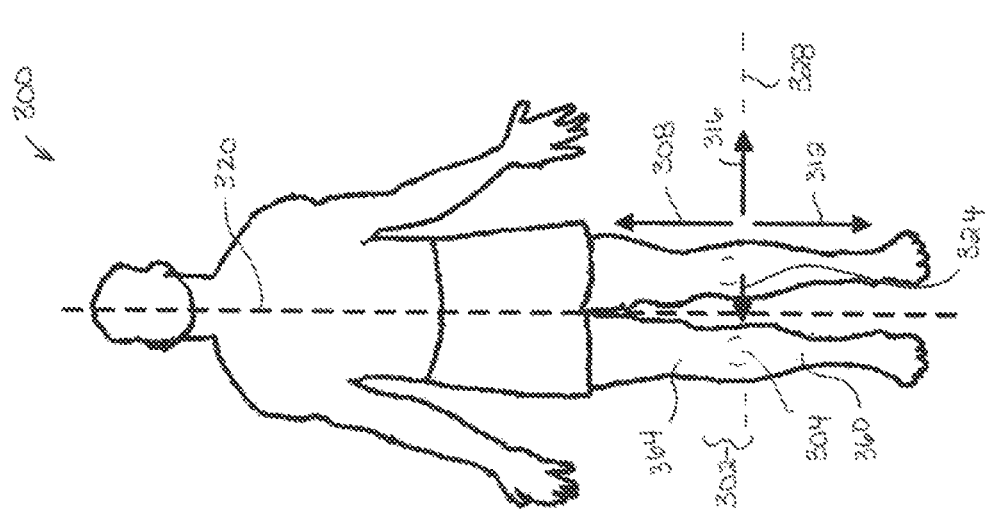
FIG. 2A shows a front schematic representation of a human body.

Referring to FIGS. 2A-2B, a schematic representation of a human body 300 is shown. As shown, human body 300 includes a knee region 302 having a kneecap 304 (also referred to as a patella), and various anatomical directions defined relative to knee region 302.

As used herein and in the claims, knee region 302 and knee rehabilitation system 100 (FIG. 1) may be described with reference to a proximal direction 308 (e.g. directed upwardly from knee region sagittal centerline 310), a distal direction 312 (e.g. directed downwardly from knee region sagittal centerline 310), a lateral direction 316 (e.g. directed away from body centerline 320), and a medial direction 324 (e.g. directed towards body centerline 320). A frontal axis 328 extends parallel to lateral and medial directions 316 and 324.

A ventral portion 336 (also referred to as a front portion or anterior portion) of knee region 302 faces generally forwardly in a ventral direction 340 (also referred to as a forward direction or anterior direction), and a dorsal portion 348 (also referred to as a rear portion or posterior portion)

of knee region 302 faces generally rearwardly in a dorsal direction 352 (also referred to as a reward direction or posterior direction). A sagittal axis 356 extends parallel to ventral and dorsal directions 340 and 352.

Figure 3:
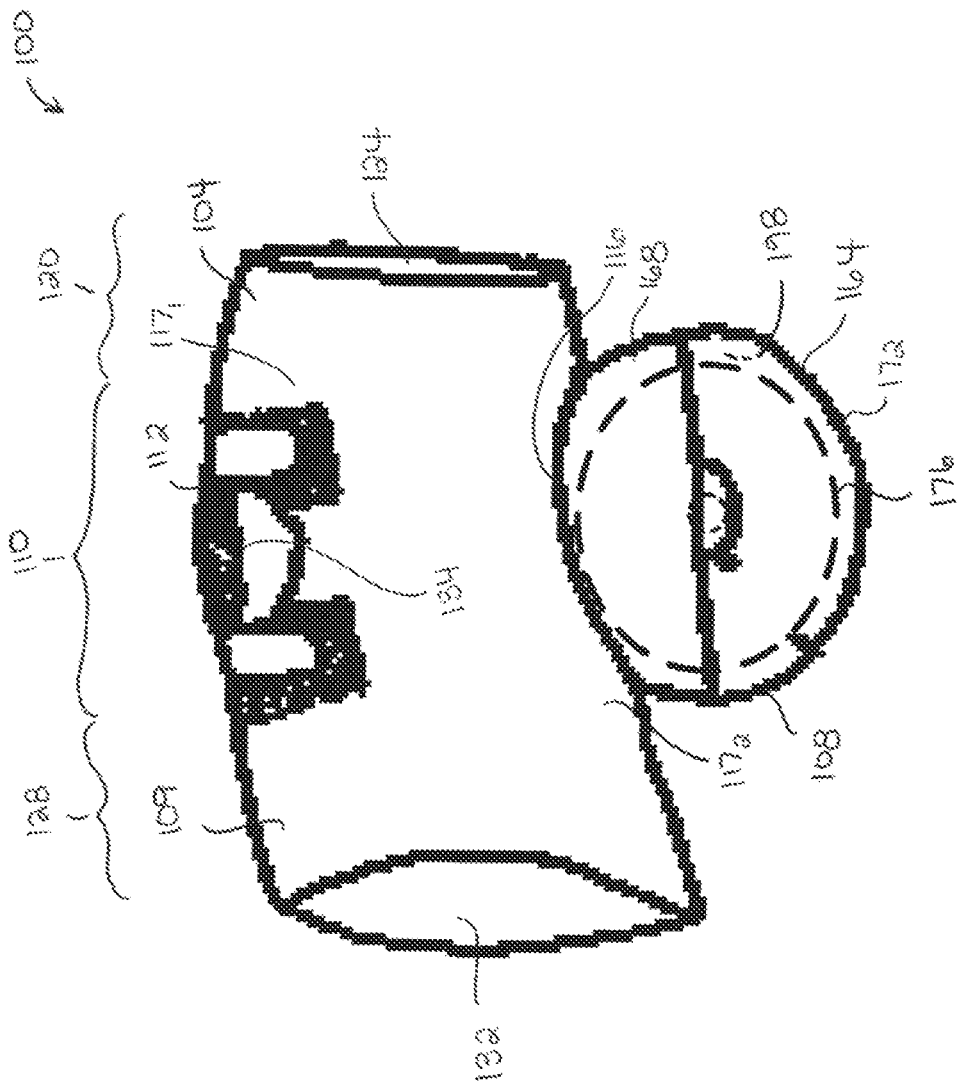
FIG. 3 shows a side perspective view of the knee rehabilitation system with a resistance member receptacle in a closed position, in accordance with an embodiment.

Reference is now made to FIG. 3. As shown, knee rehabilitation system 100 may include a knee garment 104 having a mount 108 for carrying a compressible resistance member 176. As seen in FIG. 1, a user 102 may wear knee garment 104 with the compressible resistance member mount 108 located at knee dorsal portion 348, and then exert a force 106 to compress the compressible resistance member being carried by mount 108 against a stationary surface 107 (e.g. a floor or a wall). The force required to perform the compression may be governed by the characteristic compressible resistance of the compressible resistance member. The user may strengthen their leg muscle(s) (e.g. their VMO muscle, as part of a rehabilitation program) by performing this compression several times per session, during several sessions per month (e.g. once or twice weekly).

Returning to FIG. 3, in various embodiments, knee rehabilitation system 100 may include a plurality of compressible resistance members 176, which may be interchangeably carried, one at a time, by compressible resistance member mount 108. As is described in more detail below, each compressible resistance member 176 in the plurality may be characterized as having (a) an equal (or similar) size and shape as each other compressible resistance member in the plurality, and (b) a compression resistance different from each other compressible resistance member in the plurality. This can allow the user to gradually progress to using higher resistance members 176, as their leg muscle(s) (e.g. VMO muscle) becomes stronger. By providing all of the compressible resistance members 176 with the same or similar (e.g. within 10%) size and shape, the form of the exercise (e.g. limb angles, range of motion, etc.) may remain consistent with best practices as resistance is increased by using a progressively higher resistance member 176.

Still referring to FIGS. 2A-2B and 3, knee garment 104 may have any configuration suitable for holding compressible resistance member mount 108 proximate knee dorsal portion 348. For example, knee garment 104 may include a sleeve or separate discrete dorsal and ventral panels. In the illustrated embodiment, knee garment 104 includes a sleeve that when worn encircles a user's knee region 302. This may provide a relatively large contact surface area between knee garment 104 and knee region 302, which may mitigate knee garment 104 sliding out of position on knee region 302 when performing exercises.

In some embodiments, knee garment 104 may be configured as a knee compression garment which overlays and compresses the user's knee region 302 during use. For example, knee garment 104 may be sized and shaped, and composed of a material, that exerts a pressure of at least 0.5 kPa (e.g. between 1 kPa and 8 kPa) upon knee region 302 when worn. Without being limited by theory, it is believed that the sustained compressive force to knee region 302 during exercise may improve flexion and extension, reduce incidences of injury, and stabilize joints. For example, as a compression garment, knee garment 104 may act to stabilize patella 304 thereby mitigating patellar maltracking.

Knee compression garment 104 may, in at least some embodiments, include a resiliently stretchable body 109 formed at least partially of elastic material. For example, knee compression garment 104 may be formed of elastic material extensible to at least 200% (e.g. between 200% and 400%) original length in at least one direction without breaking. This can allow knee compression garment 104 to properly fit on knee regions 302 of many different shapes and sizes. In turn, this may reduce the number of SKUs that must be manufactured and made available in order to broadly accommodate most users. Alternatively, or in addition to providing an elastic extensibility of at least 200%, the elastic material may provide knee garment 104 with a characteristic compressive pressure of at least 0.5 kPa (e.g. between 0.5 kPa and 8 kPa) to knee region 302 when worn.

Still referring to FIGS. 2A-2B and 3, in alternative embodiments, knee garment 104 may not comprise a compression garment, but may instead comprise a garment which provides substantially no compressive force to the user's limb (e.g. knee) when worn thereon (also referred to as a "non-compression garment"). For example, knee garment 104 may exert a compressive force of less than 0.5 kPa (e.g. 0 kPa to 0.5 kPa) upon knee region 302 when worn. As compared with a knee compression garment, a non-compression knee garment 104 may be more easily pulled over knee region 302 and more comfortable for an individual suffering from certain knee impairments. In some cases, knee garment 104 may be formed of a substantially inelastic material. For example, knee garment 104 may be composed of a substantially inelastic material extensible to less than 150% (e.g. between 100% and 150%) before breaking.

Irrespective of whether knee garment 104 is a compression garment or a non-compression garment, in various embodiments, knee garment 104 may include a knee portion 110 having a ventral portion 112 and a dorsal portion 116. When knee garment 104 is worn by the user, ventral portion 112 is positioned over knee ventral portion 336, and dorsal portion 116 is positioned behind knee dorsal portion 348. As shown, ventral portion 112 and dorsal portions 116 may together encircle knee region 302 when knee garment 104 is worn.

In at least some embodiments, ventral portion 112 and dorsal portion 116 may each include a fabric panel 117. When knee garment 104 is worn, fabric panel $117_1$ of ventral portion 112 may cover (i.e. overlay) at least a portion (or all) of knee ventral portion 336, and fabric panel $117_2$ may cover (i.e. overlay) at least a portion (or all) of knee dorsal portion 348. Fabric panels $117_1$ and $117_2$ may be discrete panels connected to each other, or integrally formed. In the illustrated embodiment, fabric panels 117 form a sleeve having a tubular shape, which is pulled over the user's leg to encircle knee region 302. An advantage of the sleeve configuration is that it may be easily pulled over the user's leg with few or no adjustments required for size.

Figure 4:
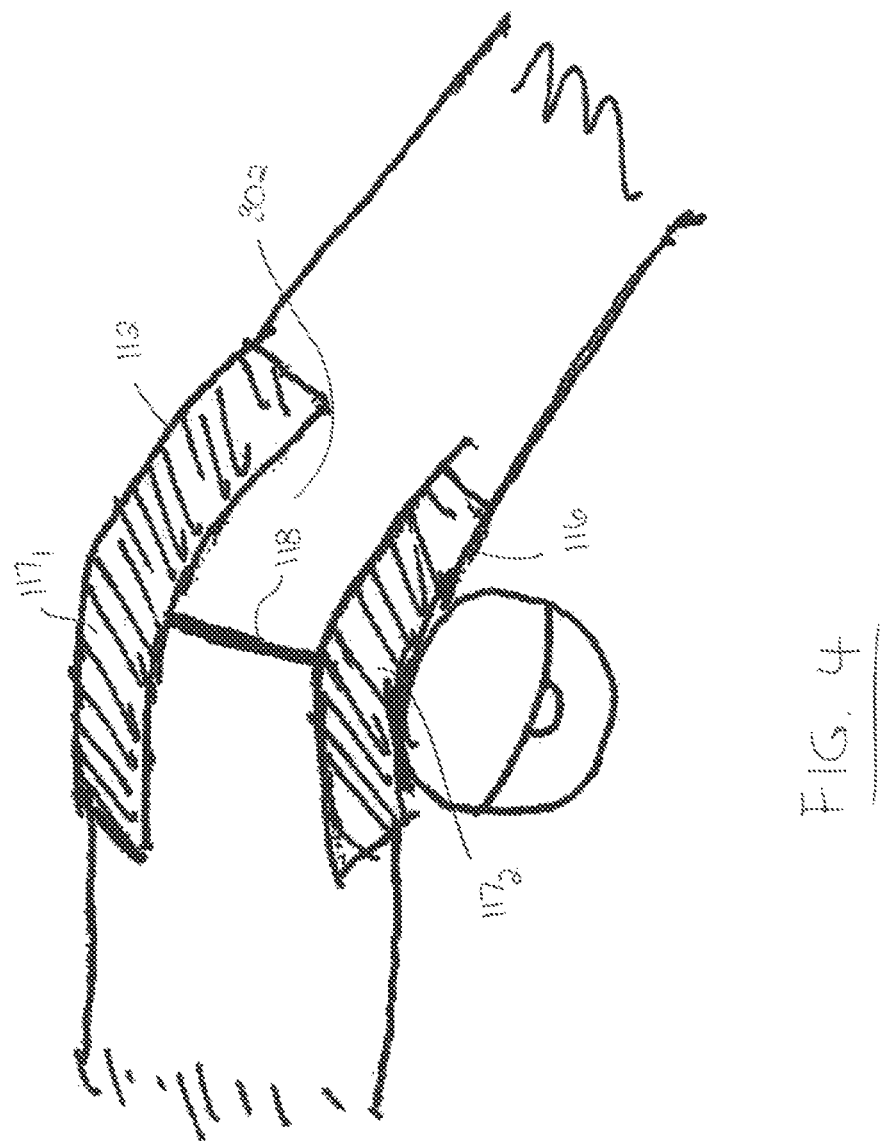
FIG. 4 shows a knee rehabilitation system worn on a leg in accordance with another embodiment.

Referring to FIGS. 2A-2B and 4, alternative embodiments may include ventral and dorsal portions 112 and 116 formed from spaced apart panels (e.g. fabric panels) which are connected to each other by a suitable attachment member 118. The attachment member 118 may comprise, for example, a strap (e.g. string, belt, or band) as shown. An advantage of using spaced apart panels 117 for ventral and dorsal portions 112 and 116 is that it may provide better airflow and visibility to knee region 302 during exercises.

Attachment members 118 may have a fixed length, or an adjustable length. For example, a fixed length attachment member 118 may be inelastic and connected at each end to a different one of panels 117. An adjustable length attachment member 118 may be elastic or inelastic, and may include a length adjustment device (e.g. a clasp or buckle). By providing an adjustable length, attachment member 118 can allow knee garment 104 to be fitted onto knee regions 302 of many sizes. In turn, this may reduce the number of SKUs that must be manufactured and made available in order to broadly accommodate most users. As an example, elastic attachment members 118 may be formed from elastic material extensible to at least 150% (e.g. between 150% and 400%) original length without breaking.

Reference is now made to FIGS. 2A-2B and 3. In some embodiments, knee garment 104 may include a first leg portion 120 connected to the knee portion 110. When knee garment 104 is worn, first leg portion 120 may extend distally from knee portion 110 to engage (e.g. overlay) at least a portion of the user's lower leg 360 (e.g. the crus), which is located distally of knee region 302. As shown, first leg portion 120 may include a distal opening 124 sized to receive lower leg 360. Engagement between first leg portion 120 and lower leg 360 may help mitigate knee garment 104 slipping out of position when performing exercises.

Alternatively, or in addition to first leg portion 120, knee garment 104 may include a second leg portion 128 connected to knee portion 110. When knee garment 104 is worn, second leg portion 128 may extend proximally from knee portion 110 to engage (e.g. overlay) at least a portion of the user's upper leg 364 (e.g. the thigh) located proximally of knee region 302. Second leg portion 128 may include a proximal opening 132 sized to receive upper leg 364. Where knee garment 104 includes both of first and second leg portions 120 and 128, knee portion 110 may be located between and connect first and second leg portions 120 and 128. Engagement between first and/or second leg portion 120 and 128, and lower and/or upper leg 360 and 364 may help mitigate knee garment 104 slipping out of position when performing exercises.

Each of first and second leg portions 120 and 128 may have a compressive or a non-compressive configuration. For example, in a compressive configuration, the leg portion 120 or 128 may exert a compressive force of greater than 0.5 kPa (e.g. 0.5 kPa to 8 kPa) upon upper or lower leg 360 or 364 when worn. In a non-compressive configuration, leg portion 120 or 128 may exert a compressive force of less than 0.5 kPa (e.g. 0 to 0.5 kPa) upon upper or lower leg 360 or 364 when worn. In embodiments including both first and second leg portions 120 and 128, both portions 120 may have a compressive or non-compressive configuration, or one may have a compressive configuration and the other a non-compressive configuration.

Optionally, knee garment 104 may also include an inner lining 134 having anti-slip properties (also referred to as "anti-slip material"). Anti-slip lining 134 may further assist with stabilizing knee garment 104 on knee region 302. In some examples, anti-slip lining 134 may have a static coefficient of friction of greater than 1.0 when the material is dry.

Figure 5:
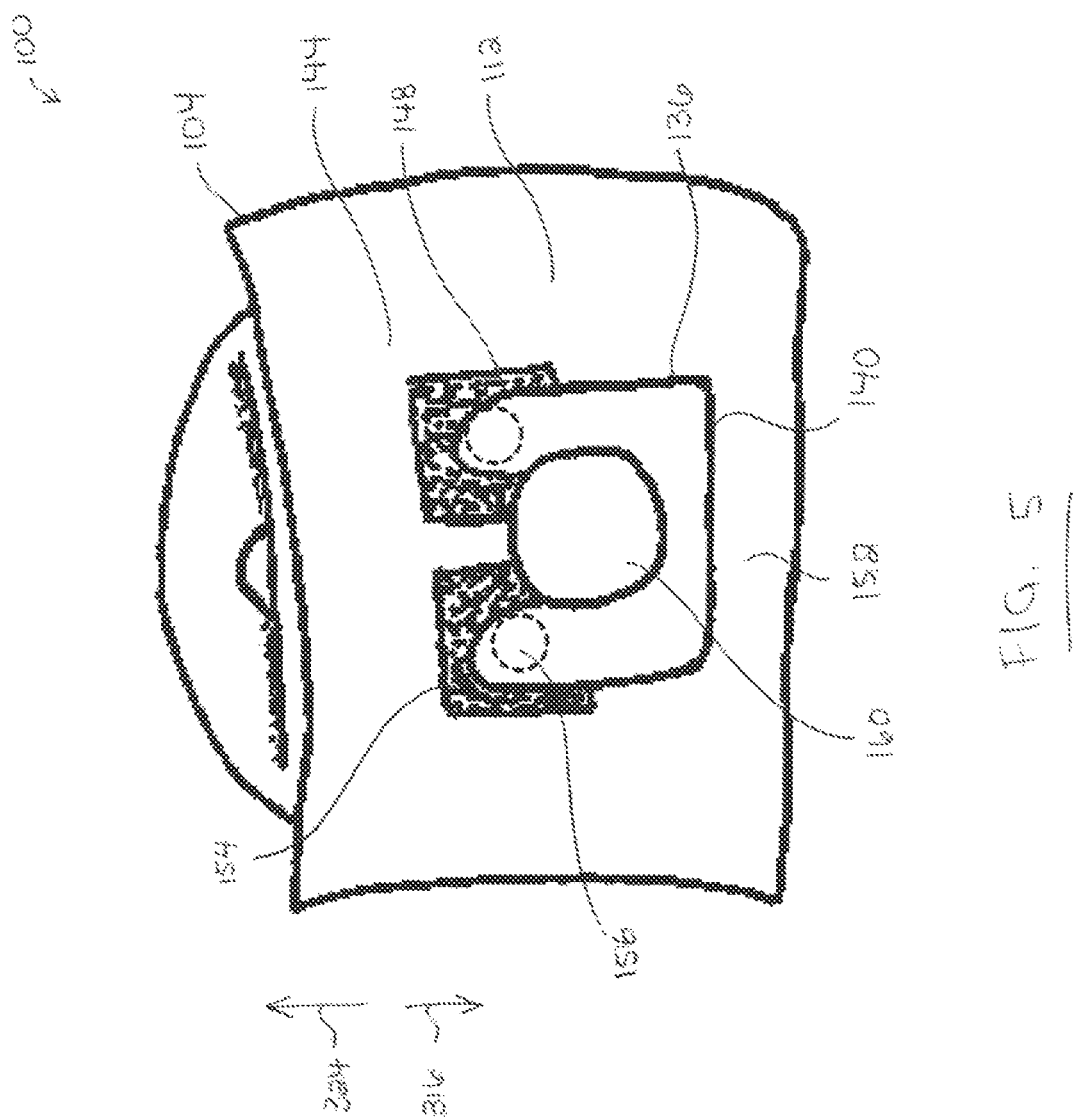
FIG. 5 shows a top plan view of the knee rehabilitation system of FIG. 3.

Referring to FIGS. 2A-2B and 5, knee garment 104 may include a patellar tracking support 136 connected to ventral portion 112. The VMO muscle is at least partially responsible for biasing the patella 304 in a medial direction during knee movements. Users having a poor strength in their VMO muscle may suffer from patellar maltracking in a lateral direction (i.e. patella 304 may move laterally out of position). Patellar tracking support 136 may improve medial tracking of a user's patella 304, which may mitigate patellar maltracking when performing exercises while wearing knee garment 104. Patellar tracking support 136 may have any configuration suitable for providing medial patellar tracking. In the illustrated embodiment, patellar tracking support 136 includes a first support end 140 rotatably coupled to a lateral side 152 of ventral portion 112, and a second support end 148 removably coupled to a medial side 152 of ventral portion 112. In use, a user may grasp second support end 148, pull second support end 148 medially while first support end 140 pivots about lateral side 152, and then fasten second support end 148 to medial side 144. This sequence of actions may help patellar tracking support 136 to engage the user's patella 304, and to adjust for patella of various sizes.

Second support end 148 may be removably connected to ventral portion 112 in any manner that allows second support end 148 to remain connected during exercises, and to be disconnected from ventral portion 112 by the user for readjustment. For example, second support end 148 may be removably connected to ventral portion 112 using a hook and loop fastener 154 (e.g. Velcro™) as shown. An advantage of using a hook and loop fastener 154 is that it provides a connection with high shear strength to resist disconnection during exercises, and relatively low peel strength to allow user-separation of second support end 148 from ventral portion 112. Alternatively, or in addition to hook and loop fastener 154, second support end 148 may be removably connected to ventral portion 112 by a magnetic fastener 156. An advantage of magnetic fastener 156 is that it may experience little wear and tear with repeated connections and disconnections. In other embodiments, second support end 148 may be removably coupled to ventral portion 112 using, for example, buttons or snaps.

Still referring to FIGS. 2A-2B and 5, patellar tracking support 136 may be generally C-shaped, in which the C-shape is characterized by a closed C-end at first support end 140, and an open C-end at second support end 148. An advantage of using a C-shaped patellar tracking support 136 is that the C-shape may surround at least a lateral portion of the user's patella 304, and accordingly allows patellar tracking support 136 to track patella 304 medially towards its proper position.

In some embodiments, ventral portion 112 of knee garment 104 may include a patellar opening 160. When knee garment 104 is worn by the user, patellar opening 160 aligns with, and receives, the user's patella 304. In this way, patellar opening 160 may help support patella 304 in proper alignment while performing exercises.

As illustrated, in embodiments where knee garment 104 includes both patellar tracking support 136 and patellar opening 160, patellar tracking support 136 may surround at least a portion of patellar opening 160.

In alternative embodiments, knee garment 104 does not include one or both of patellar opening 160 and patellar tracking support 136. This may simplify the design of knee garment 104, whereby knee garment 104 may be less expensive to manufacture.

Returning now to FIGS. 2A-B and 3, compressible resistance mount 108 may have any configuration suitable for mounting a compressible resistance member 176 at a location directly behind knee dorsal portion 348. In some embodiments, compressible resistance mount 108 may include a resistance member receptacle 164 (e.g. a pocket) that is sized and shaped to receive one of a plurality of interchangeable compressible resistance members 176. An advantage of using a receptacle is that the compressible resistance member may not be required to have its own mounting hardware in order to attach to knee garment 104 (i.e. the compressible resistance member is simply received in receptacle 164). This may reduce the design complexity and manufacturing cost associated with each compressible resistance member 176. In turn, this may substantially reduce the cost of a knee rehabilitation system 100, particularly where system 100 includes a plurality of such compressible resistance members 176.

Figure 6:
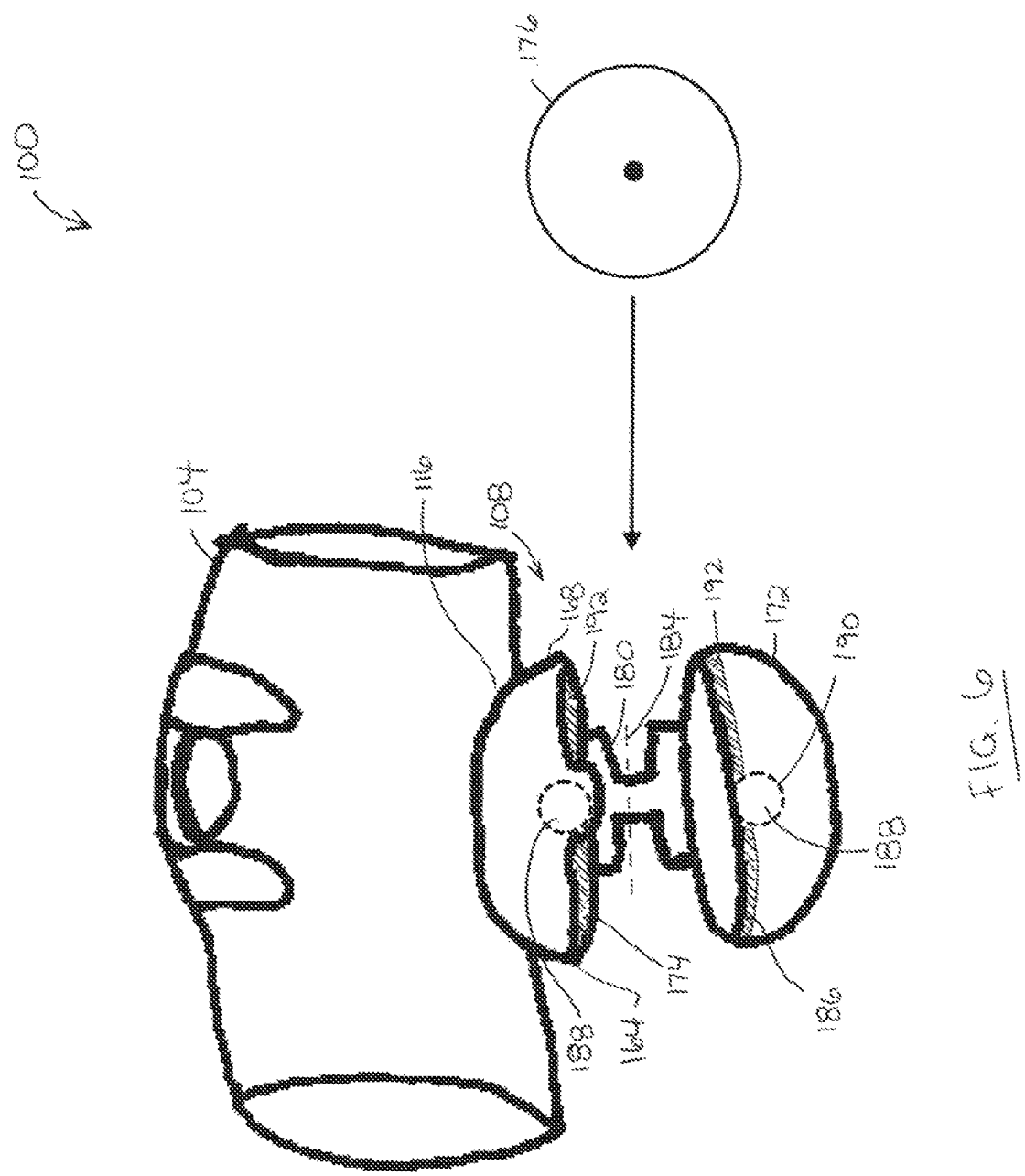
FIG. 6 shows a side perspective view of the knee rehabilitation system of FIG. 3, with the resistance member receptacle in an open position.

FIG. 6 shows resistance member receptacle 164 in an open position in accordance with an embodiment. As shown, resistance member receptacle 164 may include a first shell portion 168 and a second shell portion 172. In the illustrated example, first shell portion 168 is attached (e.g. permanently attached) to knee garment dorsal portion 116, and second shell portion 172 is movably relative to first shell portion 168 between the open position (FIG. 6) and a closed position (FIG. 3).

In the open position (FIG. 6), resistance member receptacle 164 may define an opening 174 sized to receive a single compressible resistance member 176. In the closed position (FIG. 3), first and second shell portions 168 and 172 bound an inner receptacle cavity 198 sized to hold a compressible resistance member 176.

Referring to FIG. 6, second shell portion 172 may be movably connected to first shell portion 168 in any manner. For example, second shell portion 172 may be rotatably connected (e.g. hingedly connected) to first shell portion 168, or removably connected to first shell portion 168. A rotatable connection 180 may prevent misplacing second shell portion 172 when the resistance member receptacle 164 is in the open position. The persistent connection 180 (which may be referred to as a 'hinge') between first and second shell portions 168 and 172 may be formed in any manner that allows second shell portion 172 to rotate between the open and closed positions. For example, a portion of first shell portion 168 may be sewn to a portion of second shell portion 172, a strap 180 (e.g. string, belt, or band) may join first shell portion 168 and second shell portion 172, or first and second shell portions 168 and 172 may be integrally formed.

Rotatable connection 180 may permit second shell portion 172 to rotate (e.g. pivot) relative to first shell portion 168 about a fixed or variable pivot axis. In the illustrated embodiment, connection 180 allows second shell portion 172 to pivot relative to first shell portion 168 about pivot axis 184. Pivot axis 184 may extend in any direction. In the illustrated example, pivot axis 184 extends substantially parallel to knee garment dorsal portion 116. This may permit second shell portion 172 to open in a lateral or medial direction away from knee region 302 (FIGS. 2A-2B), which may help prevent the user's leg from interfering with opening resistance member receptacle 164. In other embodiments, second shell portion 172 may open in another direction (e.g. in a proximal or distal direction).

Figure 7:
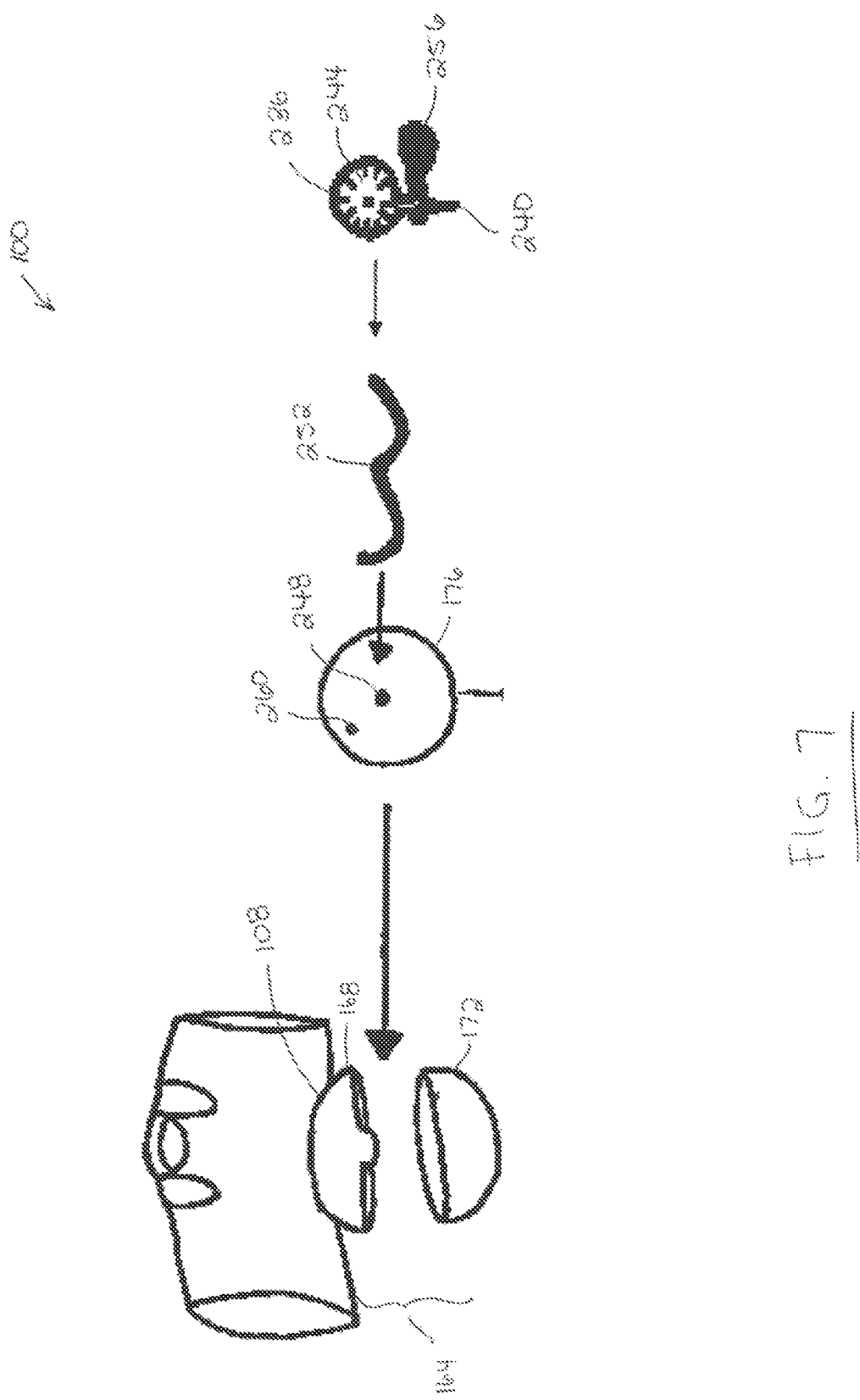
FIG. 7 shows an exploded view of the knee rehabilitation system of FIG. 1, in accordance with an embodiment.

FIG. 7 shows an alternative embodiment in which resistance member receptacle 164 is openable by completely detaching second shell portion 172 from first shell portion 168. An advantage of this design is that it may mitigate the user's leg from interfering with the opening of second shell portion 172, and it may mitigate second shell portion 172 from interfering with the reception of compressible resistance member 176 in first shell portion 168.

Irrespective of whether second shell portion 172 is rotatably or detachably connected to first shell portion 168, first and second shell portions 168 and 172 may be removably connected in any manner which reliably secures the contained compressible resistance member 176 in the closed position.

Returning to FIG. 6, in some embodiments, resistance member receptacle 164 may include a hook and loop closure 186 that releasably retains receptacle 164 in the closed position. For example, first and second shell portions 168 and 172 may include complimentary hook and loop panels 192. As shown, panels 192 may circumscribe at least some (or all) of receptacle opening 174. An advantage of using a hook and loop closure 186 is that it can provide high shear strength which may reliably secure receptacle 164 in the closed position, and relatively low peel strength that allows the user to selectively open receptacle 164.

Alternatively, or in addition to hook and loop closure 186, resistance member receptacle may include magnetic closure 190 that releasably retains receptacle 164 in the closed position. For example, first and second shell portions 168 may include complementary members 188, one of which is a magnet and the other a magnet or magnetically attractable element (e.g. ferromagnetic element). An advantage of using a magnetic closure 190 is that it may experience little wear and tear as receptacle 164 is opened and closed repeatedly over time.

Alternatively, or in addition to a magnetic and/or hook and loop closure, resistance member receptacle 164 may include one or more (or all) of buttons, snaps, or zippers to releasably secure the first and second shell portions 168 and 172 in the closed position.

Referring to FIG. 3, when resistance member receptacle 164 is in the closed position, first and second shell portions 168 and 172 border (e.g. define, surround, or bound) an inner cavity 198. Inner cavity 198 may be sized to hold no more than one (i.e. less than two) interchangeable compressible resistance members 176. Preferably, inner cavity 198 is sized to substantially immobilize a compressible resistance member 176 held therein. This may mitigate the compressible resistance member 176 moving out of alignment with knee ventral portion 336 (FIG. 2B) to an extent that it impairs properly performing exercises. For example, inner cavity 198 may have a volume in the closed position that is within 25% of a volume of any one of compressible resistance members 176. Where compressible resistance members 176 are inflated or inflatable (as discussed in further detail below), inner cavity 198 may have a volume in the closed position that is within 25% of the volume of any one of the compressible resistance members 176 at their prescribed inflation pressure.

First and second shell portions 168 and 172 may have any shape that is suitable to carry a compressible resistance member 176 in the closed position. As shown, at least one of first and second shell portions 168 and 172 may be concave. An advantage of this design is that it may permit a compressible resistance member 176 to be consistently located within the concave shell portion 168 or 172 when mounting the compressible resistance member 176. In the illustrated example, both of shell portions 168 and 172 are concave. As shown, this may permit compressible resistance member 176 to protrude from shell portions 168 and 172 when in the open position, which may make compressible resistance member 176 easier to handle during mounting and dismounting of the compressible resistance member 176. In some embodiments, first and second shell portions 168 and 172 may collectively define an inner cavity 198 having a shape (i.e. in the closed position) which complements (e.g. conforms to) the shape of the compressible resistance member 176. This may provide a tight fit for the compressible resistance member 176 within inner cavity 198 which may help to immobilize the compressible resistance member 176.

Still referring to FIG. 3, resistance member receptacle 164 may be formed from any material suitable for securing a compressible resistance member 176 within internal cavity 198. For example, receptacle 164 may include flexible material that can deform to permit compressible resistance member 176 to compress during exercises. In the illustrated embodiment, one or both of shell portions 168 and 172 may be flexible.

In some embodiments, receptacle 164 may include resiliently stretchable material (i.e. elastic material) which may be configured to expand to accommodate compressible resistance member 176 within inner cavity 198. For example, receptacle 164 may exert compressive pressure upon a contained compressible resistance member 176. This may help to substantially immobilize compressible resistance member 176 within closed receptacle 164. Alternatively or in addition, this may permit resiliently stretchable receptacle 164 to conform to the size and shape of compressible resistance member 176. This may promote proper alignment of the compressible resistance member 176 behind knee dorsal portion 348 (FIG. 3B) during exercise. In some examples, the resiliently stretchable material of receptacle 164 may be extensible to at least 150% (e.g. 150% to 400%) original length without breaking.

In alternative embodiments, receptacle 164 may be formed from non-stretchable material (i.e. inelastic material). This may mitigate any difficulty attributable to stretching receptacle 164 to accommodate compressible resistance member 176 therein. For example, one or both of shell portions 168 and 172 may be substantially inelastic. In some examples, an inelastic portion 168 or 172 may be extensible to less than 125% (e.g. 100% to 125%) original length without breaking.

In some embodiments, receptacle 164 may include rigid material. For example, one of first and second shell portions 168 and 172 may be composed of rigid material, while the other portion 172 or 168 is composed of flexible material. The rigid portion 168 or 172 may provide superior immobilization of compressible resistance member 176, while the flexible portion 172 or 168 allows the compressible resistance member 176 to compress during exercise.

Still referring to FIG. 3, receptacle 164 may be composed of substantially closed material (e.g. a continuous fabric panel), or an open material (e.g. having a plurality of openings, such as netting or similar). A closed material may have a percentage open area of less than 10% (e.g. 0% to 10%). An advantage of using a closed material is that it may prevent debris (e.g. dirt or dust) from entering inner cavity 198 when in the closed position. An open material may have a percentage open area of greater than 35% (e.g. 35% to 95%). An open material may provide easier access to compressible resistance member 176 when receptacle 164 is in the closed position (e.g. to inflate or measure an internal pressure of compressible resistance member 176, as described below). Both of shell portions 168 and 172 may be composed of closed material, both of shell portions 168 and 172 may be composed of open material, different ones of shell portions 168 and 172 may be composed of closed material and open material, or each of shell portions 168 and 172 may include both closed and open materials.

While resistance member receptacle 164 has been illustrated as a two-piece assembly (e.g. having first and second shell portions 168 and 172), in alternative embodiments, receptacle 164 may be composed of a single shell portion (e.g. a single piece assembly). For example, the single shell portion may define an inner cavity 198 having an opening that can be expanded to admit a compressible resistance member 176, and contracted to retain the compressible resistance member 176. For example, the opening may be elastically expandable, and/or associated with a drawstring. The single piece configuration may provide a simpler design that is less expensive to manufacture.

In some embodiments, compressible resistance member mount 108 may not include a resistance member receptacle 164. For example, compressible resistance member mount 108 may cooperate with a complimentary mount provided on compressible resistance member 176 to secure the compressible resistance member 176 on knee garment 104. An advantage of this design is that the compressible resistance member 176 may be more quickly and easily engaged and disengaged from the compressible resistance member mount 108. In some examples, compressible resistance member mount 108 and the complimentary mount on compressible resistance member 176 may together provide a magnetic, hook and loop, and/or snap connection.

Figure 8:
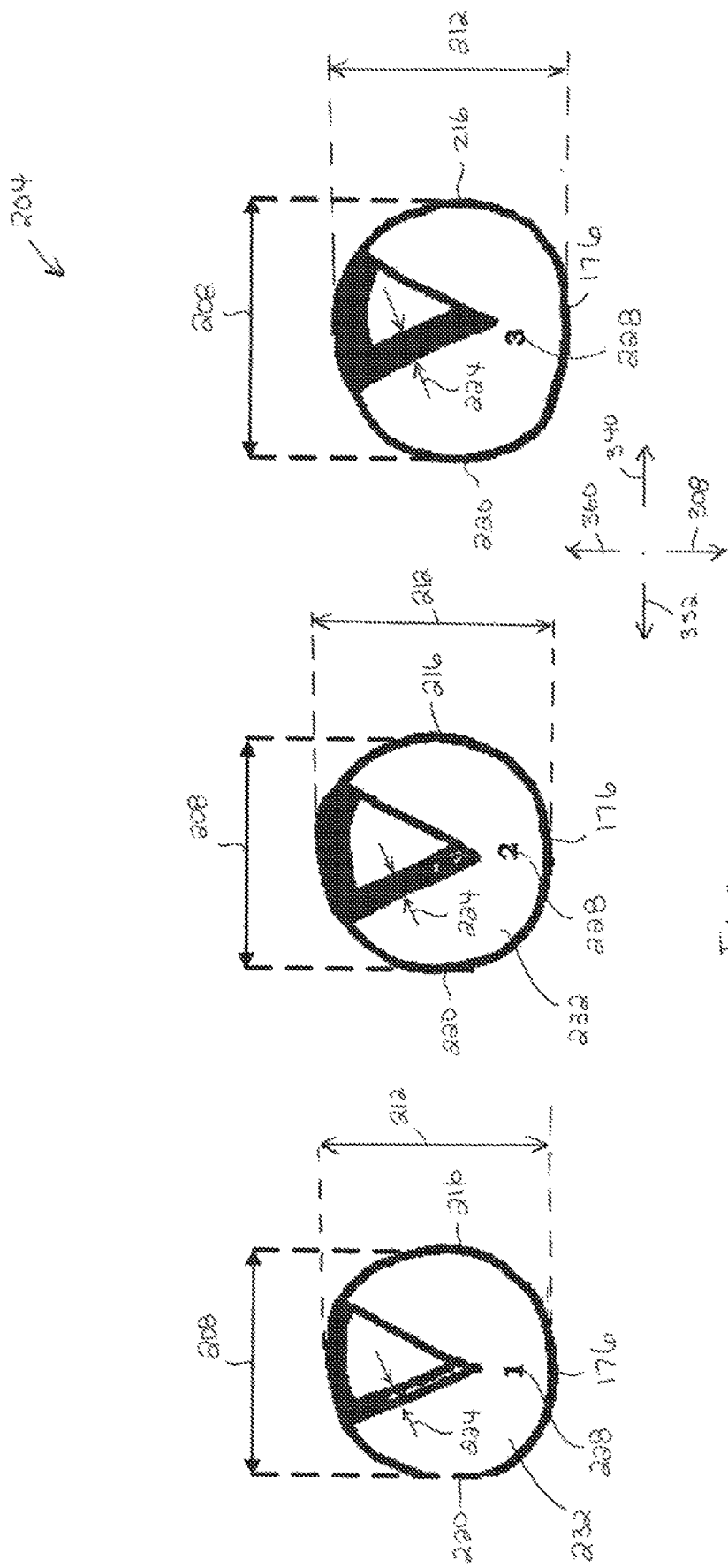
FIG. 8 shows a set of three compressible resistance members, each one having a substantially spherical shape, and each one having a section cutaway to illustrate wall thickness, in accordance with an embodiment.

Referring to FIG. 8, knee rehabilitation system 100 (FIG. 1) may include a plurality 204 of compressible resistance members 176. Each compressible resistance member 176 in the plurality 204 may have: (a) the same size and shape as each other compressible resistance member 176 in the plurality 204; and (b) a compression resistance different from each other compressible resistance member 176 in the plurality 204. This may permit compressible resistance members 176 of progressively greater compressible resistance to be used in accordance with a rehabilitation program while maintaining a constant size of compressible resistance member 176 for consistency of the exercise.

Figure 9:
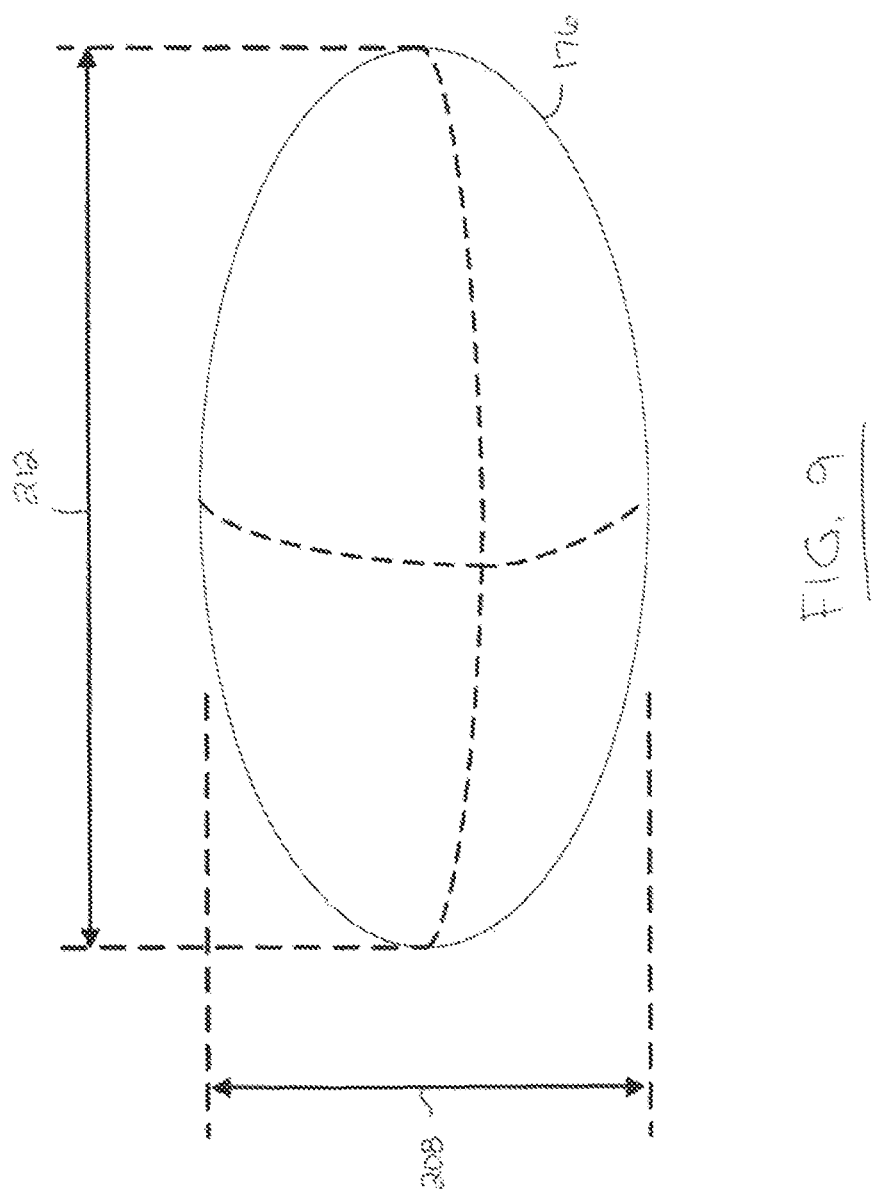
FIG. 9 shows a perspective view of a compressible resistance member having an oblate ellipsoid shape, in accordance with an embodiment.

Compressible resistance member 176 can have any shape suitable for compression in performing rehabilitative knee exercises. In the illustrated example, each compressible resistance members 176 in the plurality 204 has an ellipsoidal shape (e.g. a substantially spherical shape) of substantially the same size (e.g. the same or similar sagittal width 208). An advantage of using ellipsoidal shaped compressible resistance member 176 is that it may challenge the user to maintain lateral stability during compressive exercises, which may further the rehabilitative goals of the exercise regimen. FIG. 9 shows an example of a compressible resistance member 176 having a non-spherical ellipsoidal shape (e.g. an oblate ellipsoidal shape). As shown, the compressible resistance member 176 may have a relatively larger lateral width 212, which may improve lateral stability when compressing resistance member 176 during exercise.

Returning to FIG. 8, each compressible resistance member 176 may include a front end 216, a rear end 220, and a sagittal width 208. In the case of a spherical compressible resistance member 176, sagittal width 208 is equal to the lateral width 212. Compressible resistance member 176 may have any sagittal width 208 suitable for performing compressive exercises in accordance with a rehabilitation program (e.g. for VMO strengthening). For example, sagittal width 208 may be at least 5 inches (e.g. from 5 to 9 inches). This may allow the compressible resistance member 176 to compress by a sufficient travel distance to perform exercises effective for strengthening knee-related muscles (e.g. the VMO muscle). Further, compressible resistance member 176 may have any lateral width 212 suitable to distribute pressure across a lateral width of knee dorsal portion 348 (FIG. 2B). For example, lateral width 212 may be at least 5 inches (e.g. 5 inches to 15 inches or more). This may permit compressible resistance member 176 to span the lateral width of knee dorsal portion 348 (FIG. 2B) of most users. A compressible resistance member 176 having a narrower lateral width 212 may exert pressure upon a sub-region of knee dorsal portion 348 (FIG. 2B) during exercise, which may be uncomfortable and affect the effectiveness of the rehabilitation exercise.

Figure 10:
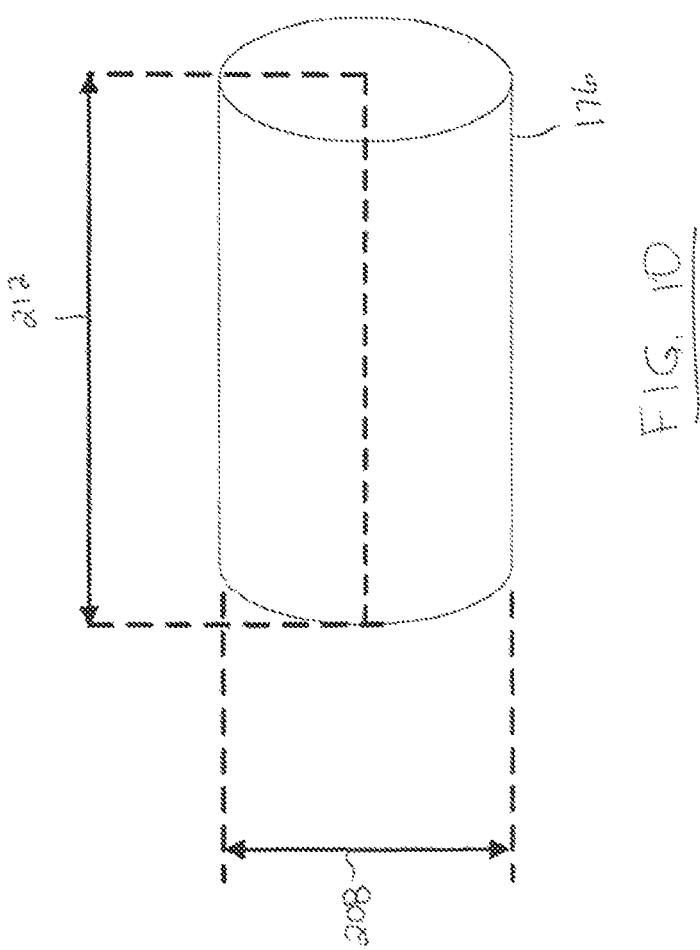
FIG. 10 shows a compressible resistance member having a cylindrical shape, in accordance with an embodiment.

FIG. 10 shows a compressible resistance member 176 having a non-ellipsoidal shape. As shown, compressible resistance member 176 may have a substantially cylindrical shape characterized by a sagittal diameter 208 and a lateral width 212. As compared with an ellipsoidal shape, the cylindrical shape may make contact with a stationary surface (e.g. wall or floor) across substantially the entire lateral width 212. This may permit compressible resistance member 176 to provide superior lateral stability during exercise. In turn, this may permit the user to focus their efforts on applying a compressive force in a dorsal direction without concern of rolling laterally and causing discomfort or injury.

Figure 11:
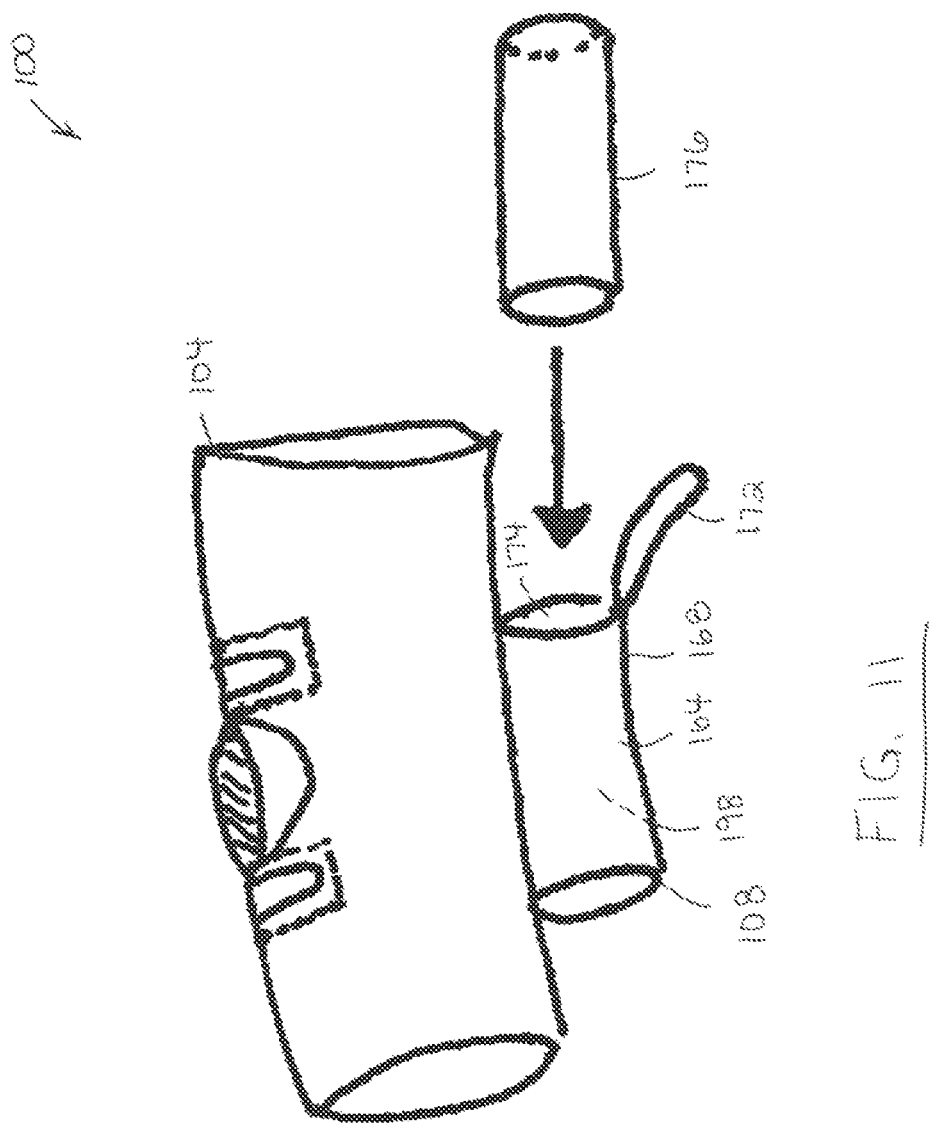
FIG. 11 shows a perspective view of a knee rehabilitation system in accordance with another embodiment.

FIG. 11 illustrates an example of a resistance member receptacle 164 sized and shaped to receive a cylindrical resistance member 176. As shown, resistance member receptacle 164 may include a first shell portion 168 having a hollow and substantially cylindrical shape, and a second shell portions 172 that defines an openable door. Second shell portion 172 may be movable relative to first shell portion 168 between open and closed positions. When second shell portion 172 is in the open position, an opening 174 is provided to admit compressible resistance member 176 into first shell portion 168. In the closed position, second shell portion 172 may close opening 174. Together, first and second shell portions 168 and 172 may define a cylindrical inner cavity 198, which conforms to the cylindrical shape of compressible resistance member 176.

Returning to FIG. 8, each compressible resistance member 176 in the plurality 204, may have a different compression resistance from every other compressible resistance member 176 in the plurality 204. Compressible resistance members 176 within the plurality 204 may have any structural differences that provide this variation in compression resistance. For example, each compressible resistance member 176 may have a different wall thickness 224 as shown, a different inflation pressure, and/or be composed of a different material. Generally, a greater wall thickness, greater inflation pressure, or stiffer material may provide greater compression resistance all else being equal. Preferably, the variation of compression resistance is provided while maintaining a constant size among the compressible resistance members 176 in the plurality 204. This may avoid changing the form of the exercise when interchanging between compressible resistance members 176 of different compression resistance.

An advantage of varying compression resistance by variable outer wall thickness is that the plurality 204 of compressible resistance members 176 may all be made of the same material, which may simplify manufacturing and thereby reduce costs. An advantage to varying compression resistance by varying inflation pressure or material is that it may permit high compression resistance without requiring large wall thicknesses that may reduce the maximum compression distance. In the case of varying inflation pressures, compressible resistance members 176 may be made of flexible but substantially inelastic material that may inflate to a constant size at different inflation pressures. Alternatively, each compressible resistance member 176 may be made of elastic material that inflates to a particular size when inflated to a prescribed inflation pressure, where the prescribed inflation pressure is different for each compressible resistance member 176. In various embodiments, each compressible resistance member 176 in the plurality 204 may be formed of at least one of polyvinyl chloride (PVC) and rubber.

Still referring to FIG. 8, in some embodiments, each compressible resistance member 176 may include a visual indicium 228 representative of a compression resistance of that compressible resistance member 176. In some examples, visual indicium 228 may indicate the absolute compression resistance of the compressible resistance member 176 (e.g. in terms of pressure or force). In other examples, visual indicium 228 may indicate a relative compression resistance of a compressible resistance member 176 as compared to the other compressible resistance members 176 in the plurality 204. For example, visual indicium 228 may include a number or letter in a sequence of numbers or letters ordered by compression resistance of the plurality 204 of compressible resistance members 176 (e.g. "1" may identify a lowest compression resistance, "2" an intermediate compression resistance, and "3" a high compression resistance). In other examples, visual indicium 228 may be provided by a color of outer surface 232 of the compressible resistance member 176, wherein different colors represent different compression resistances, ordered according to a prescribed color order.

In order to provide a gradual progression of compressive resistance for a rehabilitation program, knee rehabilitation system 100 (FIG. 1) may include three or more compressible resistance members 176 (e.g. 3 to 50 compressible resistance members 176) having different compression resistances. This may for example, allow a user to gradually progress from using compressible resistance members 176 with lower compression resistance to compression resistance members 176 with higher compression resistance as the targeted muscle(s) gain strength. Compression resistance members 176 in the plurality 204 may differ in compression resistance by any amount suitable for providing gradual progression in accordance with a rehabilitation program. For example, any two compressible resistance member 176 within plurality 204 that are adjacent in terms of compression resistance, may have a compression resistance ratio of at least 21:20 (e.g. between 21:20 and 3:1). This may allow the compression resistance members 176 to provide stepwise changes in compression resistance that are meaningful without being so great that they are impractical.

Figure 12:
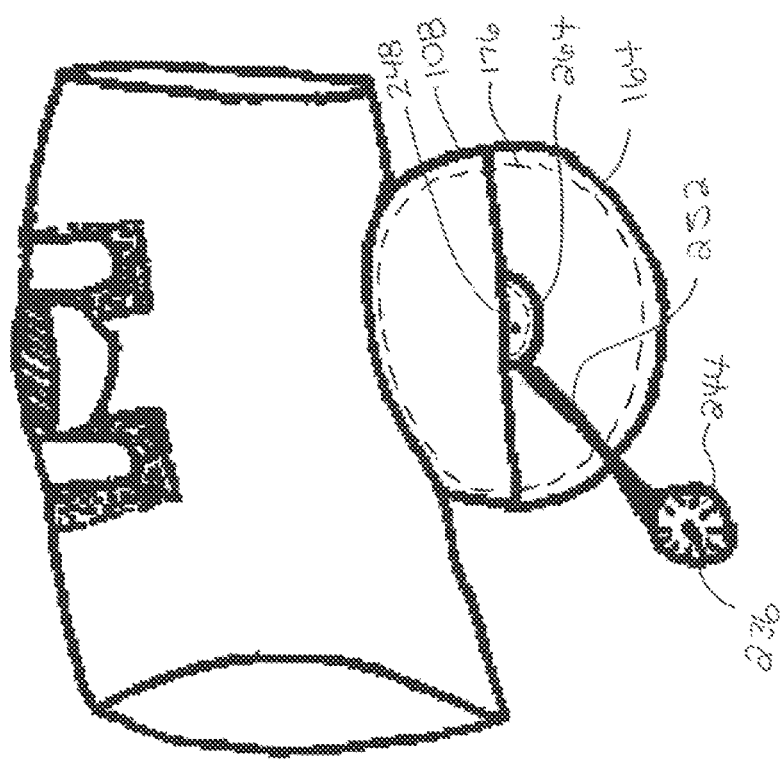
FIG. 12 shows a perspective view of the knee rehabilitation system of FIG. 1.

Reference is now made to FIGS. 7 and 12, which show a knee rehabilitation system 100 in according with an embodiment. As shown, knee rehabilitation system 100 may include a pressure gauge 236 having a gas port 240 and a display 244.

Pressure gauge gas port 240 may be positioned or positionable in fluid communication with an inner gas volume of a compressible resistance member 176 being carried by resistance member mount 108. This allows pressure gauge display 244 to display an indication of the absolute or relative change in pressure of the inner gas volume of the compressible resistance member 176 during exercise. The change in pressure may allow the user to assess the compression force they are applying to the compressible resistance member 176. For example, the user may monitor pressure gauge display 244 during exercise to verify that they are applying at least a prescribed force with each compression of compressible resistance member 176.

Pressure gauge gas port 240 (which may be referred to as a pressure gauge gas inlet) may be fluidly connected to the inner gas volume of a compressible resistance member 176 in any manner that allows the pressure gauge 236 to readout changes in pressure on display 244. In the illustrated embodiment, pressure gauge 236 may be removably fluidly connected to the inner gas volume by way of a compressible resistance member gas port 248. The removable connection may permit a single pressure gauge 236 to be used with all compressible resistance members 176 in the plurality. This may avoid the expense of providing a pressure gauge 236 for each compressible resistance member. Gas ports 240 and 248 may be directly connected, or indirectly connected (e.g. by way of an extension hose 252). Extension hose 252 may permit pressure gauge 236 to be held at a position and orientation that makes display 244 easier for the user to read during exercise (see, e.g. FIG. 1).

In alternative embodiments, pressure gauge gas port 240 may be permanently attached to a respective compressible resistance member 176 in fluid communication with the inner gas volume thereof. An advantage of using a permanent attachment is that pressure gauge 236 cannot be misplaced, and display 244 may be configured specially for the connected compressible resistance member 176.

Pressure gauge display 244 may have any configuration suitable to display an indication of pressure changes of the inner gas volume of the connected compressible resistance member 176 during exercise. For example, pressure display 244 may be a mechanical display or a digital display. As an example, a mechanical display may include a dial with a needle that moves to indicate actual or relative pressure changes. An advantage of using a mechanical display 244 is that it may not require an electrical power source. Examples of a digital display 244 include an LED, LCD, OLED, TFT, or e-paper display. Pressure gauge display 244 may display an actual pressure readout and/or a relative pressure read out (e.g. zeroed at the start of the pressure reading), in real values (e.g. in numeric pressure units) or as abstract indications (e.g. in coded numbers, coded alphabetical characters, or coded colors). For example, the user may monitor pressure gauge display 244 as they exert force upon compressible resistance member 176 with an aim of changing a displayed pressure indication from "10 psi" to "30 psi", or from "1" to "3", or from "A" to "C", or from red to green.

Optionally, pressure gauge 236 may include an inflation bulb 256. Inflation bulb 256 may be used to inflate the inner volume of a connected compressible resistance member 176 by way of gas ports 240 and 248. In this case, pressure gauge gas port 240 may function both as a gas inlet for pressure gauge 236 to take pressure readings, but also as a gas outlet to inflate the compressible resistance member 176 to a prescribed pressure. In some embodiments, the prescribed pressure may be between 20 and 80 psi. An advantage to providing an inflatable compressible resistance member 176 is that it may be inflated to a variable pressure (e.g. to vary the compression resistance, if designed to do so), it may be stored in a compact deflated configuration, and it may be reinflated to a prescribed pressure to correct for losses of gas pressure over time. As used herein and in the claims, a "size" of an inflatable compressible resistance member 176 refers to the size of the compressible resistance member 176 when inflated (e.g. to a prescribed pressure).

In other embodiments, pressure gauge 236 does not include inflation bulb 256. This may provide pressure gauge 236 with a more compact and simplified design that may be less expensive to manufacture.

In some embodiments, a compressible resistance member 176 may include a gas release valve 260. Gas release valve 260 may allow the user to selectively release gas from compressible resistance member 176. This may be useful where a user wishes to reduce the pressure of the inner gas volume of the compressible resistance member 176. For example, this can allow the user to correct for an increased gas pressure resulting from high ambient temperatures (e.g. summer heat), or to choose a lower compression resistance (e.g. in the case of a compressible resistance member 176 configured to provide variable compression resistance based upon internal gas pressure). In some cases, gas port 248 may also function as the gas release valve. In other embodiments, compressible resistance member 176 may not include a gas release valve 260.

Referring to FIG. 12, resistance member mount 108 may include an access opening 264 (shown covered by a flap) sized to accommodate pressure gauge gas port 240 or an extension hose 252. This allows pressure gauge 236 to fluidly connect with a compressible resistance member 176 located within resistance member receptacle 164. Where compressible resistance member 176 includes a gas port 248, access opening 264 may be positioned to align with gas port 248 when resistance member receptacle 164 is in the closed position. Where resistance member receptacle 164 includes an open material, a plurality of openings in the open material may provide access openings 264. This may make it easy to align resistance member gas port 248 with an access opening 264.

In some embodiments, at least a portion of resistance member receptacle 164 may be transparent. This may provide the user with visibility to the compressible resistance member 176 inside. In turn, this may make it easier to align the resistance member gas port 248 with the access opening. As used herein and in the claims, an element may be described as "transparent" where it transmits at least 50% of light in the visible spectrum.

FIG. 1 shows a user 102 wearing knee rehabilitation system 100 while performing a rehabilitation exercise in accordance with an open kinetic chain method. As shown, knee garment 104 is worn around knee region 302, with patellar opening 160 aligned with the user's patella 304, and patellar tracking support 136 surrounding at least a portion of patella 304. A compressible resistance member is mounted to knee garment dorsal portion 116 by compressible resistance member mount 108. In a seated position, the user is seen exerting a medial force (e.g. by knee extension) that compresses the compressible resistance member between the user's knee region 302 and a horizontal floor 107. As shown, the user 102 may monitor pressure gauge 236 for an indication of the medial force or pressure they apply during the exercise.

Figure 13:
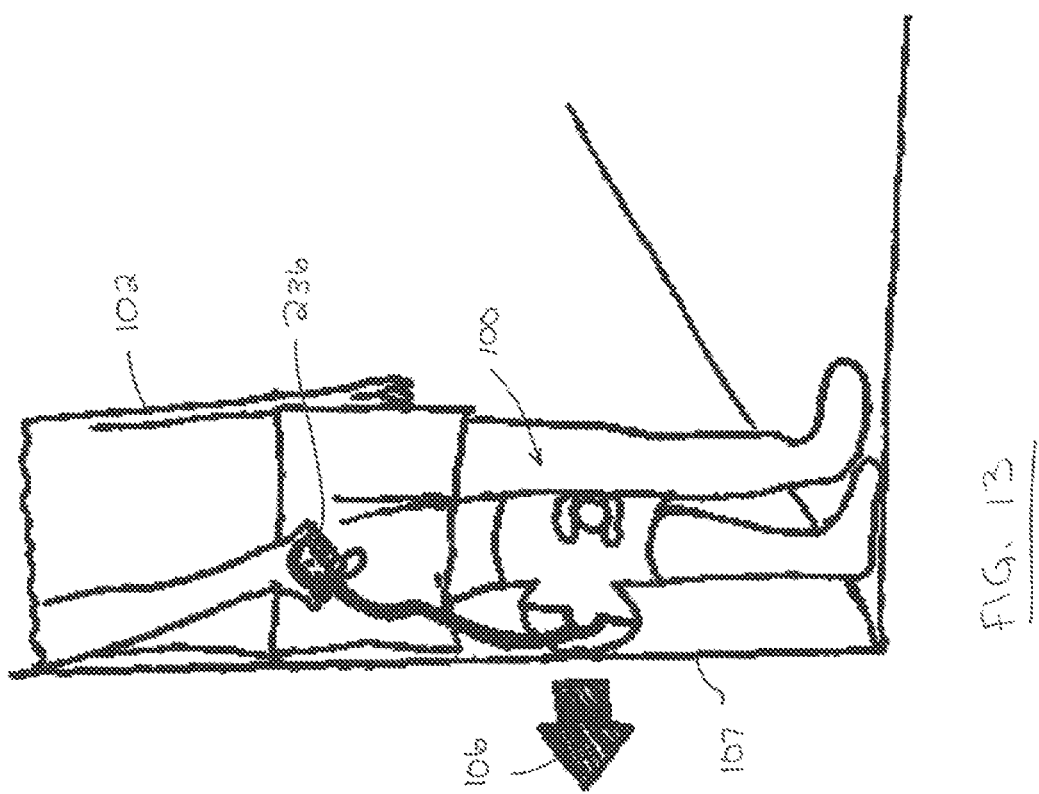
FIG. 13 shows a user wearing the knee rehabilitation system of FIG. 1 and performing an open kinetic chain rehabilitation exercise.

FIG. 13 shows user 102 wearing knee rehabilitation system 100 while performing a rehabilitation exercise in accordance with a closed kinetic chain method. As compared with FIG. 1, the user 102 is in a standing position and compresses the compressible resistance member against a vertical wall 107.

Reference is now made to FIG. 14. In some embodiments, one or more (or all) of compressible resistance members 176 may include a transmitter 268 that can transmit resistance member information 272 wirelessly to an electronic device 400. The resistance member information 272 may include any information related to compressible resistance member 176, such as for example, a member identifier 404 (e.g. representative of the compressible resistance of member 176, such as for example "#3", "orange", or "50 psi"), a pressure indication 408 (e.g. an absolute or relative change in pressure, in real terms (e.g. numerical pressure units) or coded values (e.g. numeric, alphabetical, or colored)), or both. Electronic device 400 may (i) store this information in memory, (ii) display this information on display 412, or both.

Figure 15:
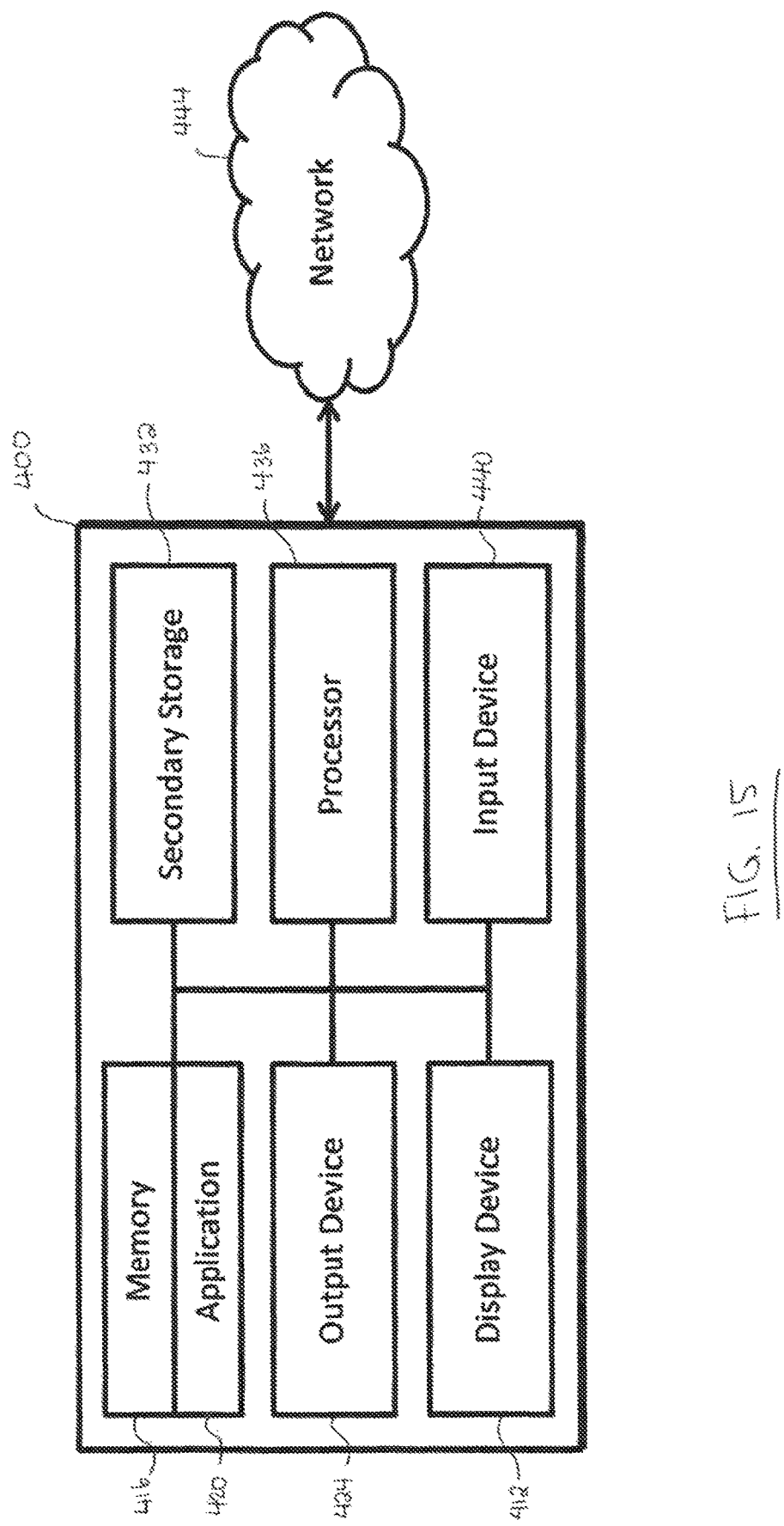
FIG. 15 is a schematic illustration of the electronic device of FIG. 14.

FIG. 15 is a schematic illustration of electronic device 400. Generally, device 400 can be a server computer, desktop computer, notebook computer, tablet, PDA, smartphone, or another computing device. In at least one embodiment, device 400 includes a connection with a network 444 such as a wired or wireless connection to the Internet or to a private network. In some cases, network 444 includes other types of computer or telecommunication networks.

In the example shown, device 400 includes a memory 416, an application 420, an output device 424, a display device 412, a secondary storage device 432, a processor 436, and an input device 440. In some embodiments, device 400 includes multiple of any one or more of memory 416, application 420, output device 424, display device 412, secondary storage device 432, processor 436, and input device 440. In some embodiments, device 400 does not include one or more of applications 420, second storage devices 432, network connections, input devices 440, output devices 424, and display devices 412.

Memory 416 can include random access memory (RAM) or similar types of memory. Also, in some embodiments, memory 416 stores one or more applications 420 for execution by processor 436. Applications 420 correspond with software modules including computer executable instructions to perform processing for the functions and methods described herein in connection with device 400. Secondary storage device 432 can include a hard disk drive, floppy disk drive, CD drive, DVD drive, Blu-ray drive, solid state drive, flash memory or other types of non-volatile data storage.

In some embodiments, device 400 stores information in a remote storage device, such as cloud storage, accessible across a network, such as network 444 or another network. In some embodiments, device 400 stores information distributed across multiple storage devices, such as memory 416 and secondary storage device 432 (i.e. each of the multiple storage devices stores a portion of the information and collectively the multiple storage devices store all of the information). Accordingly, storing data in memory (e.g. memory 416 or storage device 432) as used herein and in the claims, means storing that data in a local storage device, storing that data in a remote storage device, or storing that data distributed across multiple storage devices, each of which can be local or remote.

Generally, processor 436 can execute applications, computer readable instructions or programs. The applications, computer readable instructions or programs can be stored in memory 416 or in secondary storage 432, or can be received from remote storage accessible through network 444, for example. When executed, the applications, computer readable instructions or programs can configure the processor 436 (or multiple processors 436, collectively) to perform the acts described herein with reference to device 400.

Input device 440 can include any device for entering information into device 400. For example, input device 440 can be a keyboard, key pad, cursor-control device (e.g. mouse or trackball), touch-screen, camera, or microphone. Input device 440 can also include input ports and wireless radios (e.g. Bluetooth®, 802.11x, RFID reader) for making wired and wireless connections to external devices (e.g. resistance member transmitter 268, FIG. 14).

Display device 412 can include any type of device for presenting visual information. For example, display device 412 can be a computer monitor, a flat-screen display, a projector or a display panel (e.g. LED, LCD, TFT, or OLED display).

Output device 424 can include any type of device for presenting a hard copy of information, such as a printer for example. Output device 424 can also include other types of output devices such as speakers, for example. In at least one embodiment, output device 424 includes one or more of output ports and wireless radios (e.g. Bluetooth®, or 802.11x) for making wired and wireless connections to external devices.

FIG. 15 illustrates one example hardware schematic of device 400. In alternative embodiments, device 400 contains fewer, additional or different components. In addition, although aspects of an implementation of device 400 are described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM.

Referring to FIGS. 14 and 15, transmitter 268 may be any device suitable for transmitting resistance member information 272 to electronic device 400, directly or by way of network 444. For example, transmitter 268 may include an active device (e.g. Bluetooth™ transmitter, 802.11x transmitter, IR transmitter or cellular-wireless transmitter) or a passive device (e.g. an RFID tag). An active device may provide greater flexibility to transmit to a network 444 (e.g. as in an "internet of things" device), whereas a passive device may not require transmitter 268 to have a power source. In some embodiments, transmitter 268 sends resistance member information 272 for storage in network 444 (e.g. cloud storage), and electronic device 400 can retrieve that information from network 444. Transmitter 268 may be located internally of compressible resistance member 176, or attached externally of compressible resistance member 176. An internal transmitter 268 may mitigate interference by transmitter 268 in the functioning of resistance member 176 during exercises, whereas an external transmitter 268 may be removable (e.g. to use with another resistance member 176 or for repair or replacement).

In some embodiments, transmitter 268 includes (or is in communication with) a pressure sensor 276 positioned to sense an internal pressure of compressible resistance member 176. This allows transmitter 268 to send resistance member information 272 including pressure readings taken during exercise. This can allow a user or a third party (e.g. physician, physiotherapist, or insurance provider) to monitor progress and/or compliance with a prescribed rehabilitation program.

FIGS. 16-19 show embodiments in which a transmitter 268 is connected to an exercise device 508. Transmitter 268 may include a resistance sensor 512 to send member information 272, including sensory data (resistance readings) to electronic device 400.

Figure 18:
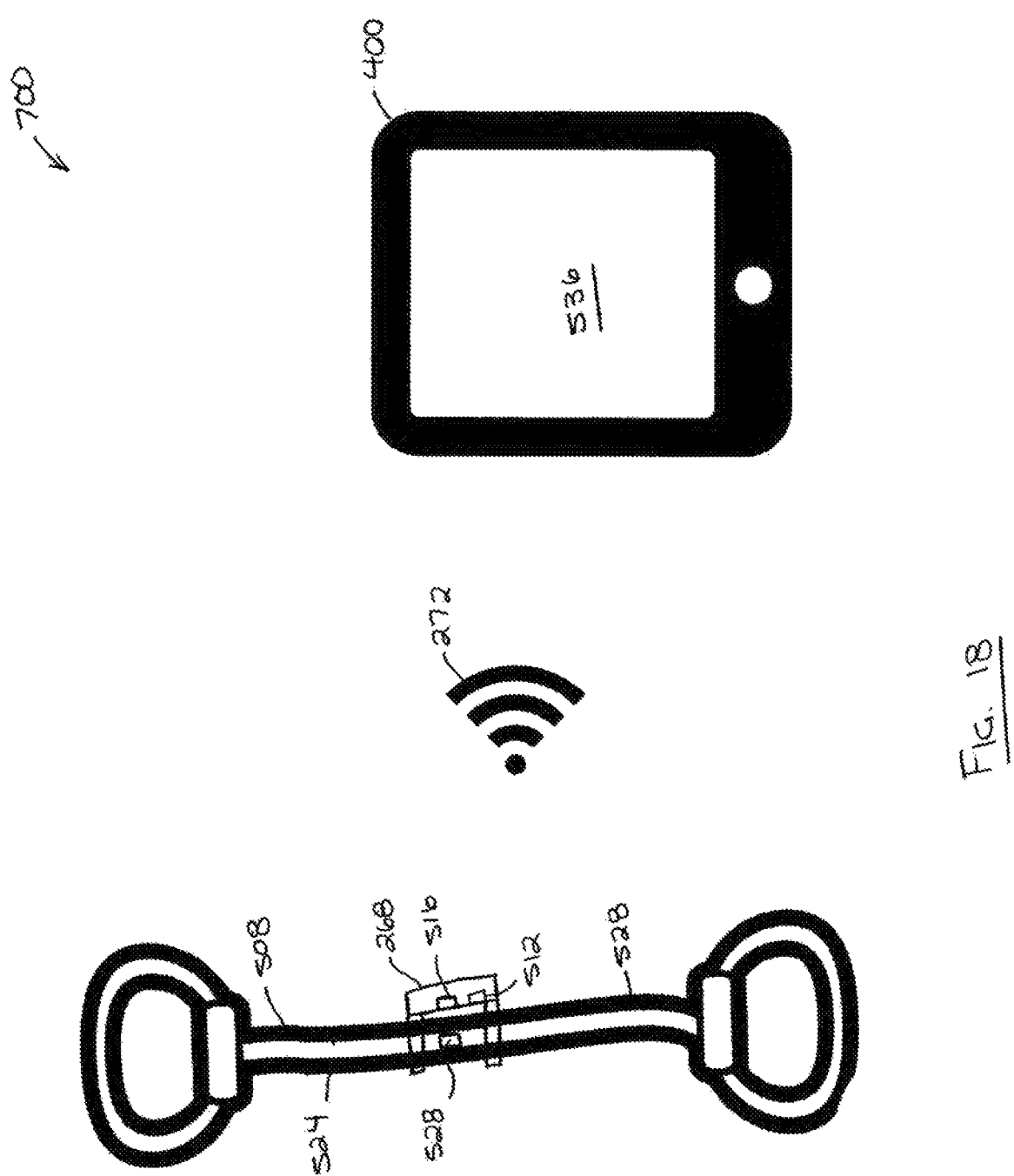
FIG. 18 is a schematic illustration of a rehabilitation system in accordance with an embodiment.
Figure 19:
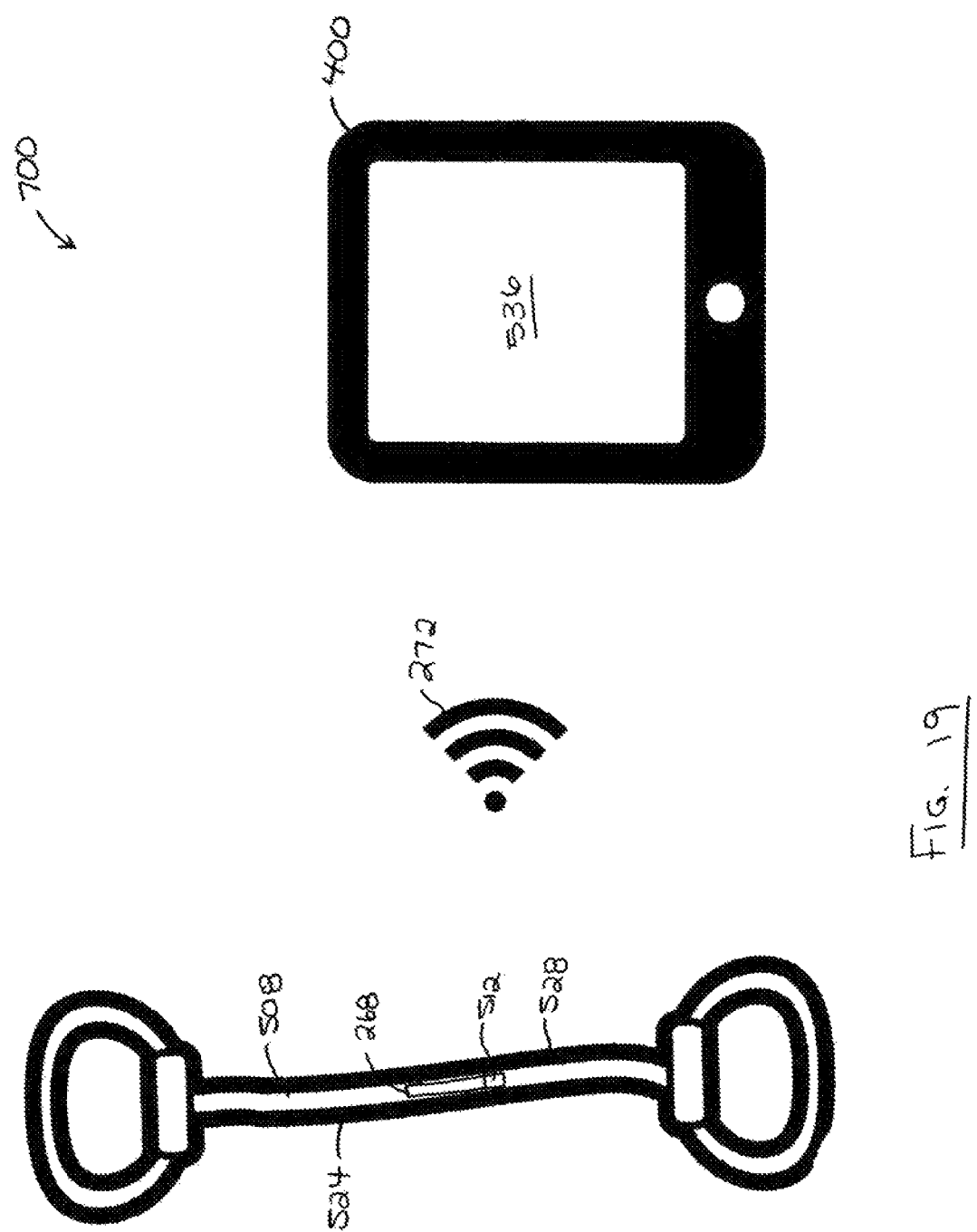
FIG. 19 is a schematic illustration of a rehabilitation system in accordance with an embodiment.

Exercise device 508 can be any device suitable for a person to perform exercises (e.g. for rehabilitation or strength training). In some embodiments, exercise device 508 may be dimensionally deformable. For example, the act of overcoming the deformation resistance of exercise device 508 may be the basis upon which exercise device 508 is used to perform exercises. FIGS. 16-17 show an example in which exercise device 508 is a compressible resistance member 176 (e.g. exercise ball). A user may compress resistance member 176 to perform exercises. FIGS. 18-19 show an example in which exercise device 508 is an elastically extensible resistance member 524 (e.g. exercise band). A user may stretch resistance member 524 to perform exercises.

Resistance sensor 512 can be any device suitable to read sensory data ("resistance measurements") indicative of a resistance met by a user of exercise device 508 during exercise. For example, resistance sensor 512 may read pressure (e.g. fluid pressure), strain, stretch (e.g. elongation or compression), stress, or force. FIGS. 16-17 show an example in which resistance sensor 512 is a pressure sensor that measures a pressure of gas within compressible resistance member 176. For example, as a user compresses compressible resistance member 176, the sensed gas pressure may rise.

FIGS. 18-19 show an example in which resistance sensor 512 is a strain, stretch, stress, and/or force sensor that measures strain, stretch, stress, or force associated with an elongation (i.e. stretching) of elastically extensible resistance member 524. For example, as a user elastically stretches resistance member 524, the sensed strain, stretch, stress, and/or force may rise.

Resistance sensor 512 may be permanently connected to the exercise device 508 (e.g. resistance sensor 512 may not be removed without causing damage to the sensor or exercise device). For example, resistance sensor 512 may be integrated into the exercise device 508 such that resistance sensor 512 cannot be moved to another exercise device 508. FIGS. 17 and 19 show examples of a transmitter 268 (including resistance sensor 512) that is non-removably connected to exercise device 508.

In other embodiments, resistance sensor 512 may be removably connected to an exercise device 508 (e.g. resistance sensor 512 may be removed for repair, recharging, or to share resistance sensor 512 between multiple exercise devices 508). FIGS. 16 and 18 show examples of transmitter 268 (including resistance sensor 512) removably connected to exercise device 508. In FIG. 16, transmitter 268 is shown connected to an exterior 232 of compressible resistance member 176 (e.g. attached to an inflation port). In FIG. 17, transmitter 268 is shown connected to an exterior 528 of elastically extensible resistance member 524. The removable connection allows transmitter 268 (including resistance sensor 512) to be used with (i.e. selectively connected to) several different exercise device 508—such as for example, several exercise devices of the same type (e.g. with differing degrees of resistance) and/or several exercise devices of different types (e.g. compressible resistance members 176 and elastically extensible resistance members 524).

In some embodiments (and not in others), a removably connected transmitter 268 may include an exercise device ID sensor 516 (e.g. RFID reader) that can read an ID element 528 (e.g. RFID tag) connected to the exercise device 508. This can allow the transmitter 268 to transmit member information 272 that based at least in part on the exercise device identification. For example, the member information 272 may include the exercise device identification (e.g. "Compressible Ball #3", or "Exercise Band #1"). Alternatively or in addition, the sensory data included in the member information 272 may be calibrated to the resistance characteristics of the identified exercise device so that the sensory data accurately reflects the resistance experienced by the user of the exercise device to which transmitter 268 is connected.

Figure 20:
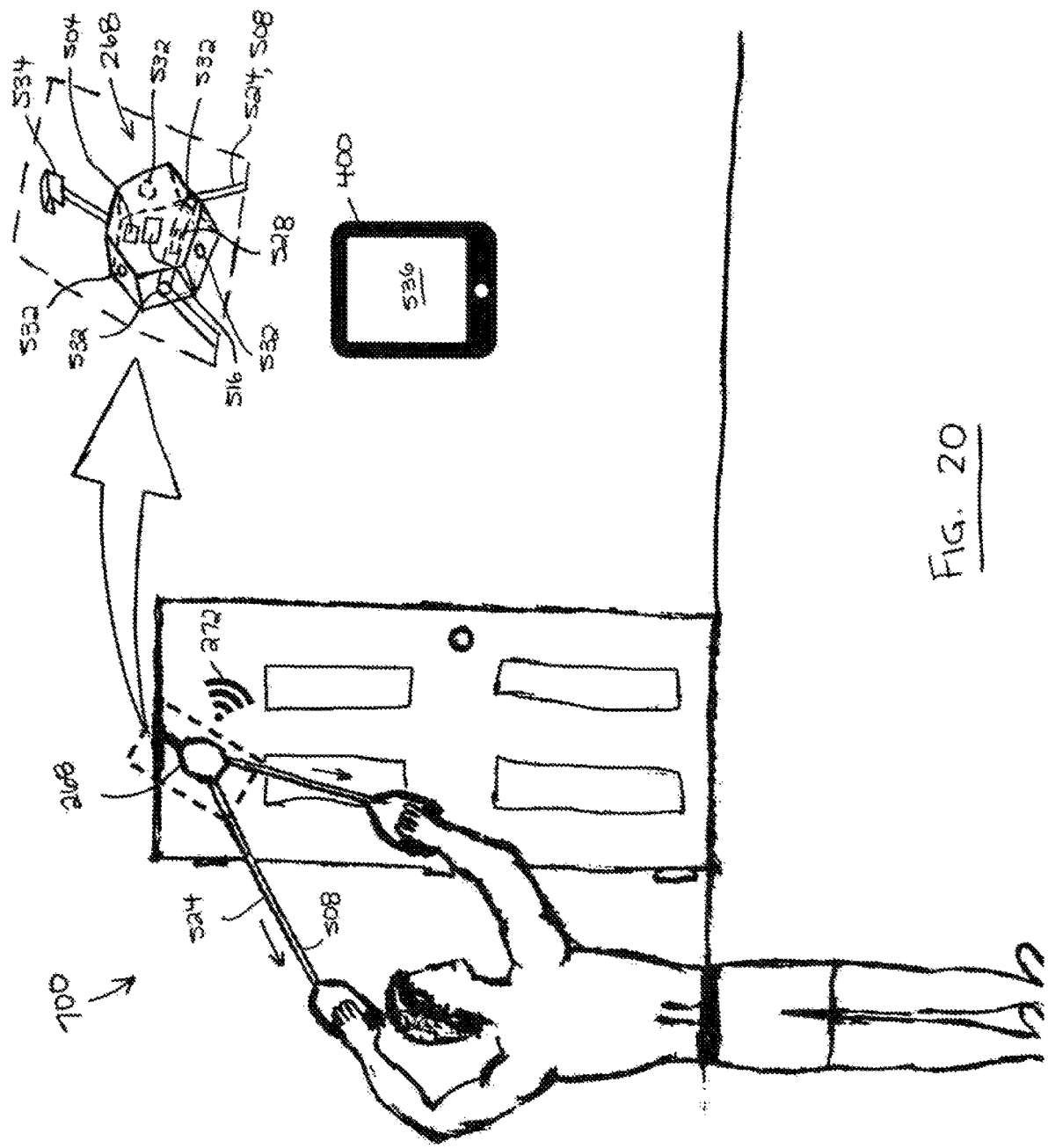
FIG. 20 is a perspective view of a user performing an exercise with a rehabilitation system in accordance with an embodiment.

FIG. 20 shows an example of a transmitter 268 that includes one or more device connections 532 for an exercise device 508. As shown, transmitter 268 may further include an anchor 534 for securing transmitter 268 to a stationary surface (e.g. a door frame as shown, the floor, a wall, etc.). In the illustrated example, device connections 532 include one or more apertures (e.g. ports) through which an exercise device (e.g. elastically extensible resistance member 524) may connect or pass. In use, transmitter 268 may experience tension as a user interacts with (e.g. stretches, compresses, pulls, or pushes) an exercise device 508 away from the anchored transmitter 268. Resistance sensor 504 may thereby read sensory data indicative of the resistance met by the user during the exercise, and transmitter 268 may send resistance member information 272 (including the sensory data) to electronic device 400.

Still referring to FIG. 20, in some embodiment, a device connection 532 may include a port to secure a hose in fluid communication with resistance sensor 504, and resistance sensor 504 may include a pressure sensor. The hose may connect at one end to a compressible resistance member 176 (FIG. 16) and at the other end to the port connection 532. In use, resistance sensor 504 may sense changes in pressure and transmitter 268 may send sensory data based on the sensed pressure values to electronic device 400 (FIG. 16).

Figure 29:
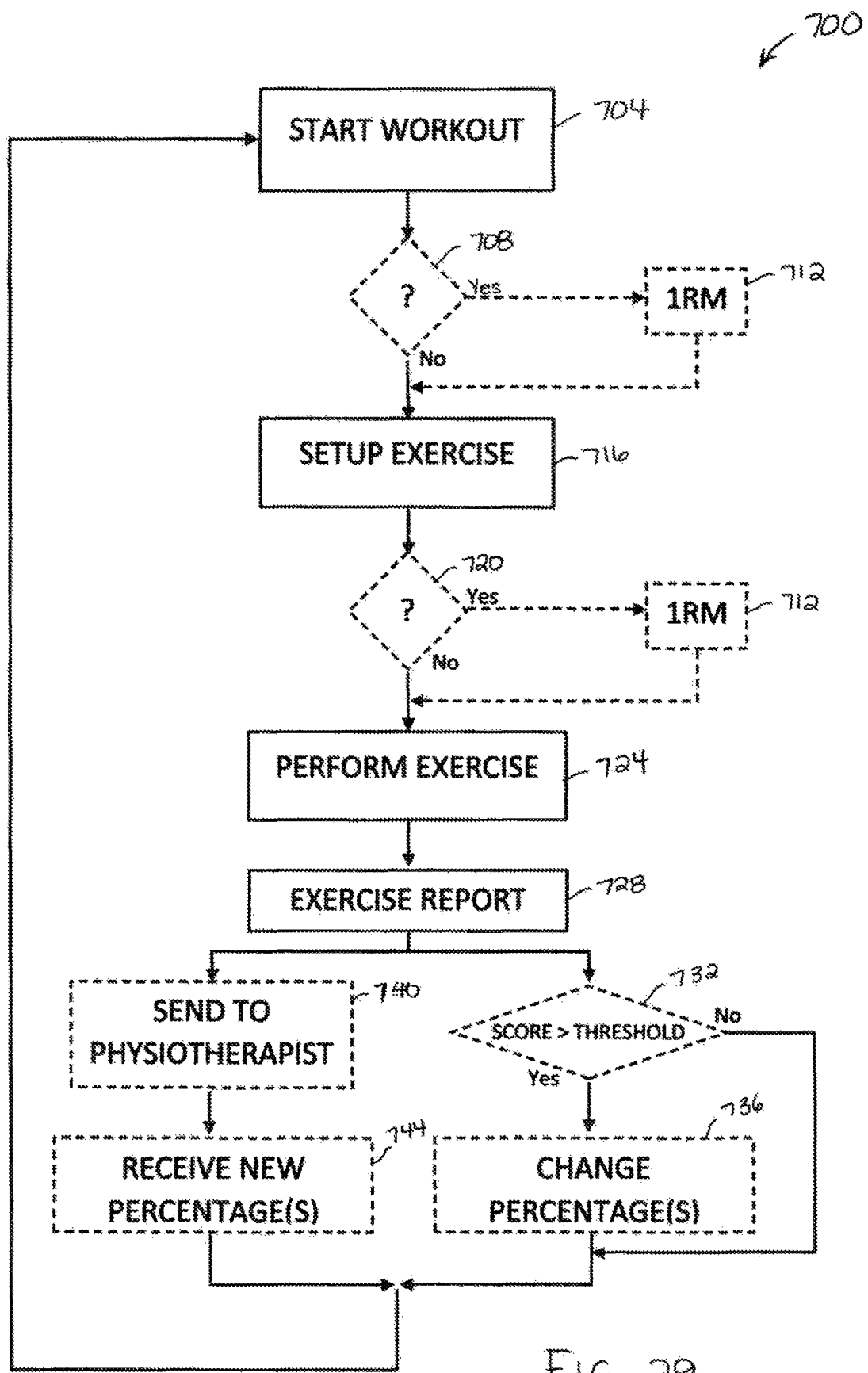
FIG. 29 is a flowchart illustrating a rehabilitation method.

Reference is now made to FIG. 29, which shows a rehabilitation method 700. As discussed below, electronic device 400 (FIG. 15) may be configured (i.e. by computer readable instructions stored in memory 416 when executed by processor(s) 436, see FIG. 15) to track user performance and compliance with prescribed exercise regimens. In use, the electronic device 400 may receive sensory information from an resistance sensor and compare the sensory information to threshold resistance(s) to determine whether to register a successful iteration (e.g. record a successful repetition) or to start an isometric-interval timer.

In the case of an injured user undergoing physiotherapy, the user may be prescribed by their physiotherapist to perform repetitions or isometric-intervals at a resistance level that is less than the user's maximum resistance capability. This is to mitigate creating or worsening an injury in performing the exercise. As described below, some embodiments of electronic device 400 (FIG. 15) may be configured to accept a threshold resistance percentage (or percentage range), measure the user's maximum resistance capability (referred to as a "one repetition maximum resistance"), and then register successful repetitions based on user exertions (as determined from sensory data received from a resistance sensor) satisfying the threshold resistance percentage (or percentage range).

Figure 21:
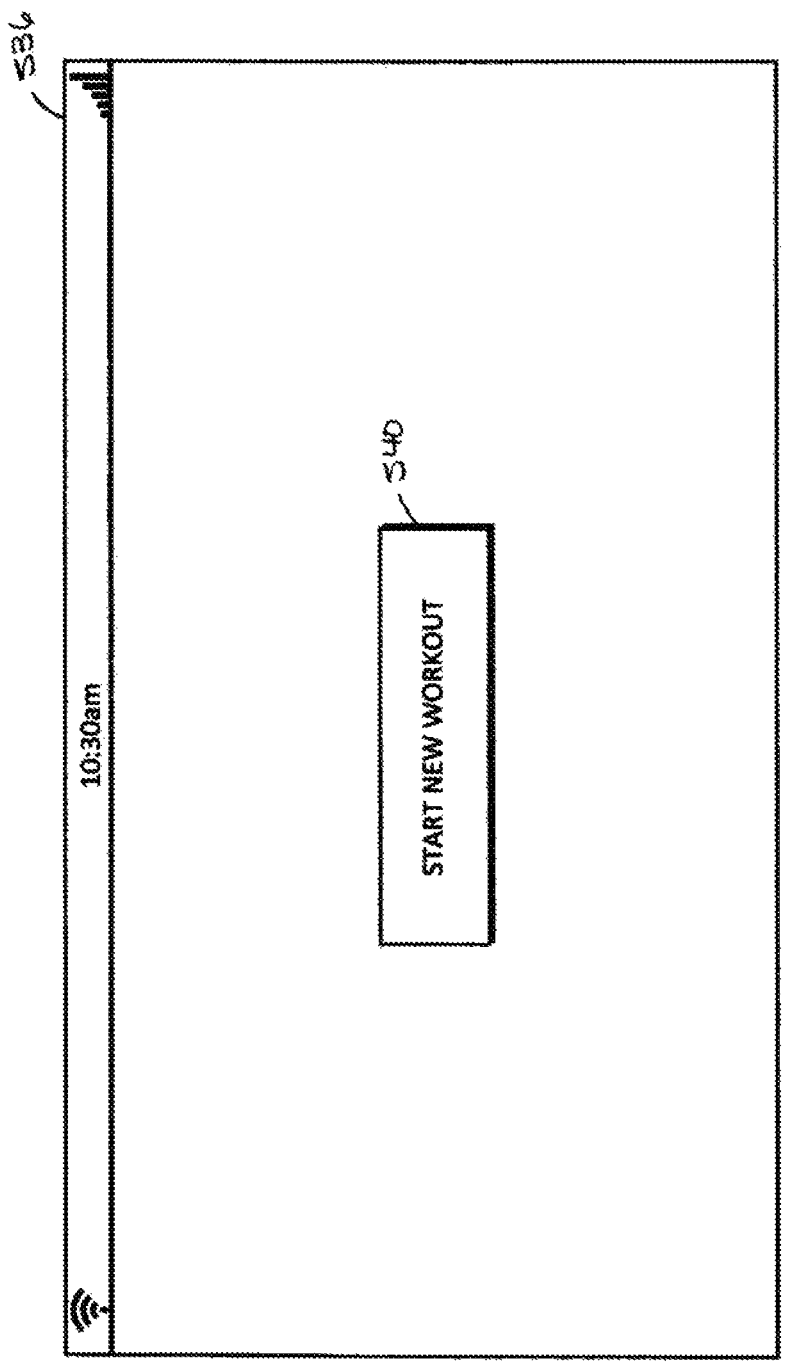
FIG. 21 is a schematic illustration of a display of a user electronic device, with a selectable option to start a workout, in accordance with an embodiment.

Reference is now made to FIGS. 16, 21, and 29. At step 704, user electronic device 400 detects an indication or user-selection to start a workout. As shown, device display 536 may allows a user to select to start a workout. As shown, display 536 may include a START WORKOUT button 540. In some embodiments, electronic device 400 may receive a direction or user indication to start a workout from the activation of device 400 (e.g. powering it on), by a wireless connection (e.g. pairing) between device 400 and transmitter 268, and/or by activation of transmitter 268.

At 708, in some embodiments, device 400 may prompt a user to perform a "one repetition maximum" in response to some logic, such as detecting that a predetermined period has elapsed since a previous workout (e.g. 1 day or 1 week), or every time that a new workout is started. A "one repetition maximum" is the maximum resistance that a user can produce for a given exercise performed with a particular exercise device. As the user's strength improves or worsens, their one repetition maximum resistance will increase or decrease. By re-measuring their one repetition maximum frequently, the exercise device 400 will guide the user to perform exercise iterations (e.g. reps or isometric-intervals) at the correct resistance level (based also on the set threshold resistance percentage, or percentage range).

Figure 22:
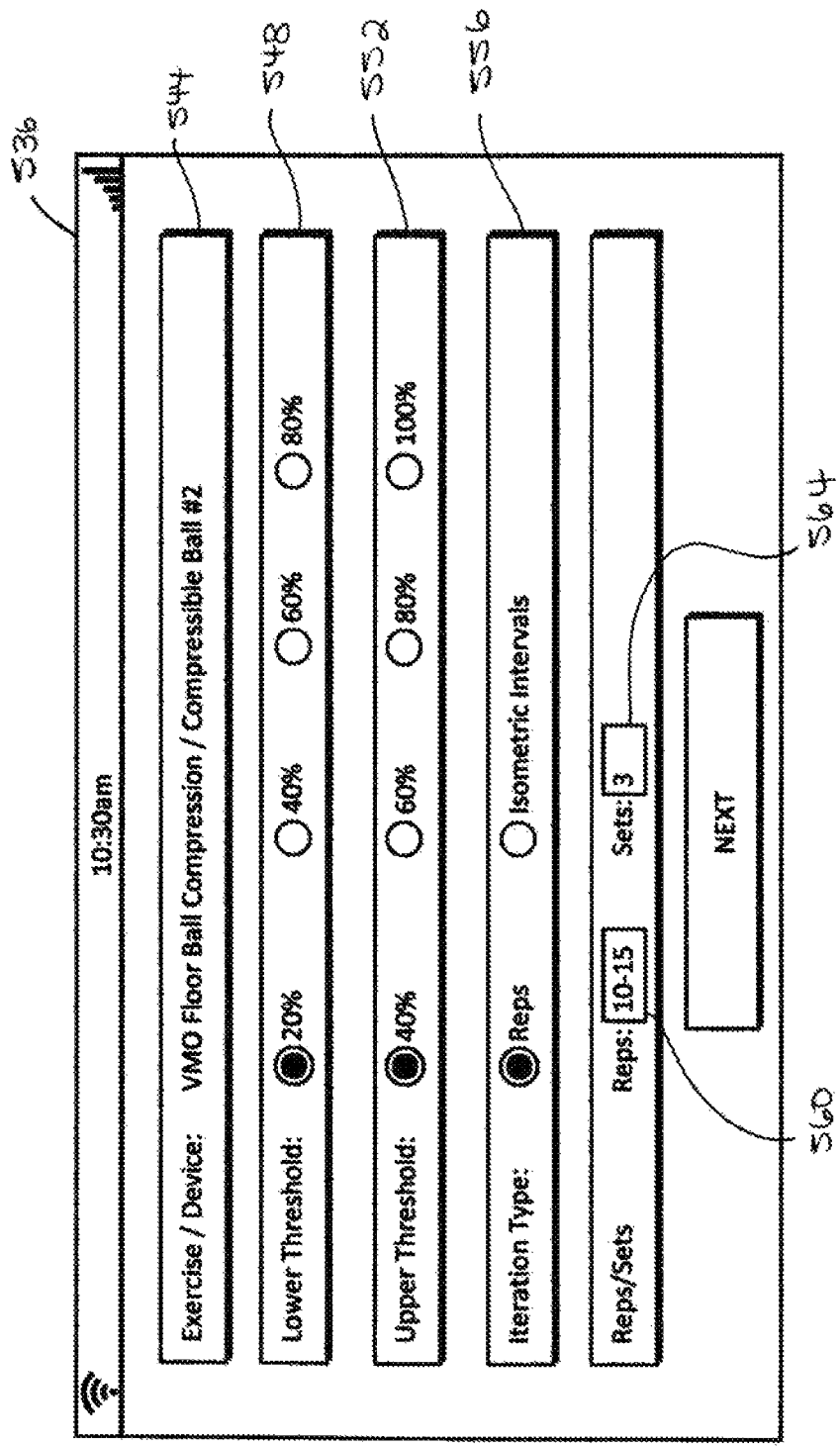
FIG. 22 is a schematic illustration of a display of a user electronic device, with selections for exercise parameters, in accordance with an embodiment.

Referring to FIGS. 16, 22, and 29, at 716 device 400 may be configured for a particular exercise. As shown, display 536 may present the user with exercise parameters selections. As shown, a user may select the exercise and exercise device 544, lower threshold percentage 548 of one repetition maximum resistance, upper threshold percentage 552 of one repetition maximum resistance, iteration type 556 (e.g.

repetitions and sets, or isometric-intervals), and the number of iterations (e.g. repetitions 560 and sets 564). In some cases, one or many of these fields may be pre-populated according to an exercise regimen stored in memory 416 (FIG. 15). In some cases, one or many of these fields (e.g. exercise device 544) may be determined by device 400 based upon an exercise device ID received in resistance member information 272 from transmitter 268.

In some embodiments, an upper threshold percentage 552 is not specified (e.g. only a lower threshold percentage 548 is specified). This may be appropriate where there is little or no risk of the particular exercise causing injury to the user on account of over-exertion.

Figure 23:
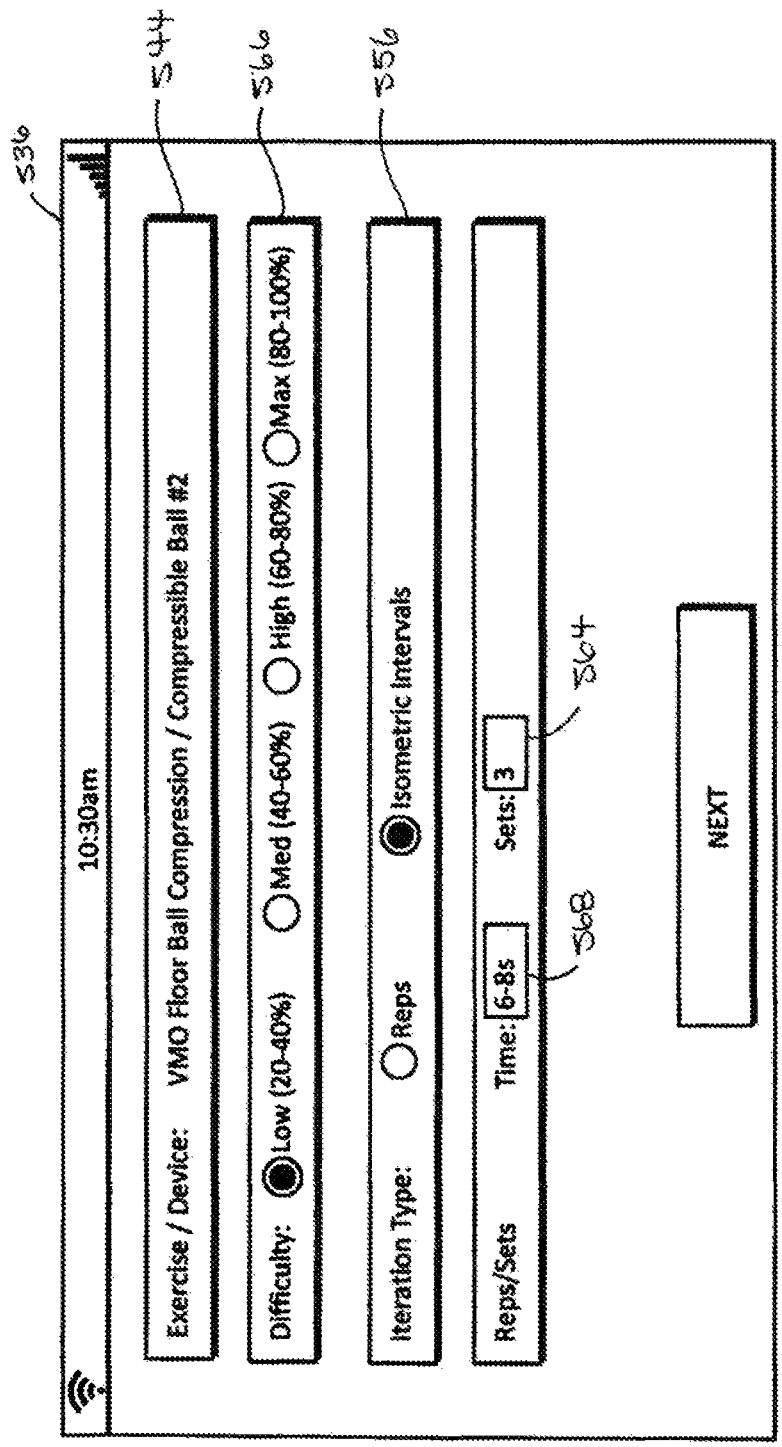
FIG. 23 is a schematic illustration of a display of a user electronic device, with selections for exercise parameters, in accordance with an embodiment.

FIG. 23 shows an example in which lower and upper threshold percentages are paired by selectable difficulty levels 566 (e.g. low difficulty 20-40%, medium difficulty 40-60%, high difficulty 60-80%, and maximum difficulty 80-100%). FIG. 23 also shows an example in which the selected iteration type 556 is isometric-intervals, and the iteration parameters include a time duration 568 for each isometric-interval.

At 720, in some embodiments, device 400 may prompt a user to perform a "one repetition maximum" in response to some logic, such as each time a user exercise is started, or every N-times a particular exercise is started.

Figure 24:
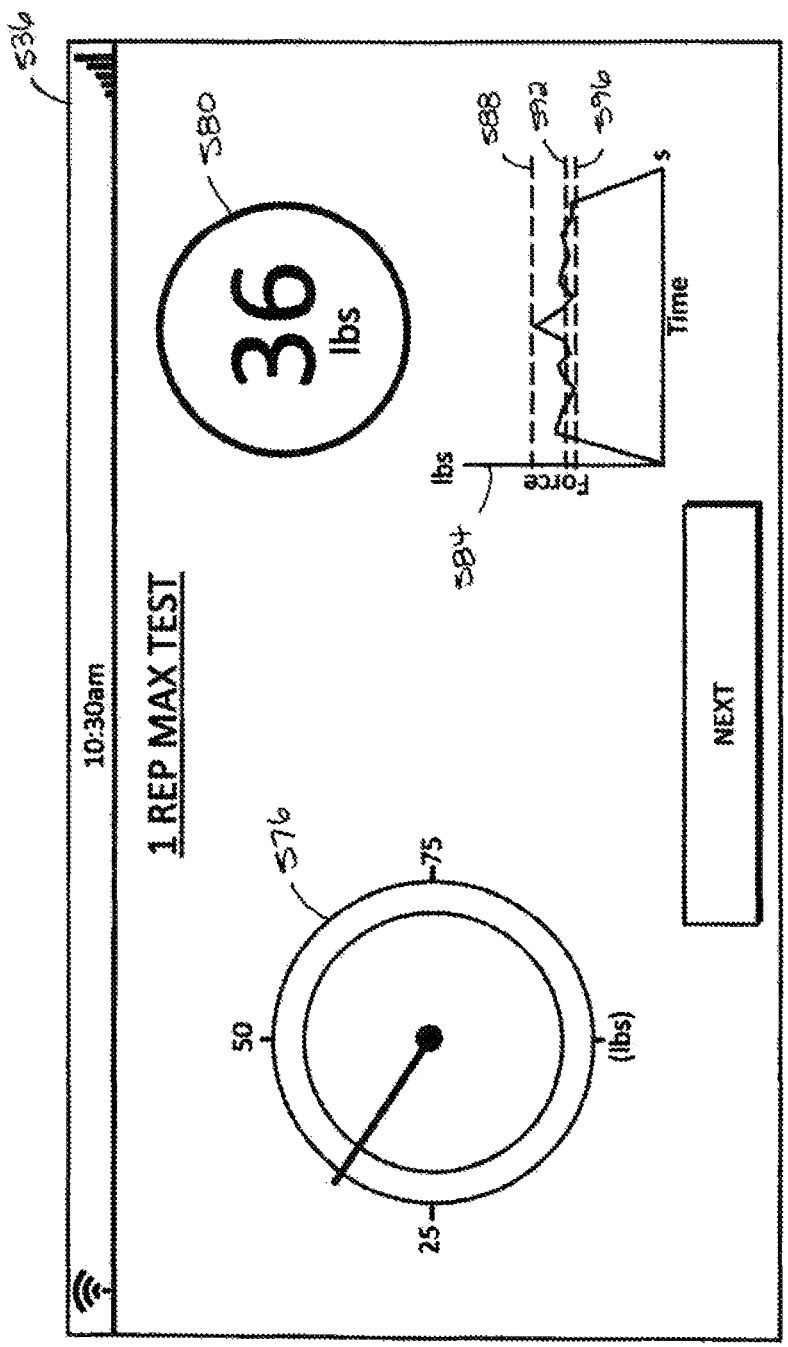
FIG. 24 is a schematic illustration of a display of a user electronic device, with a prompt to perform a one repetition maximum, in accordance with an embodiment.
Figure 25:
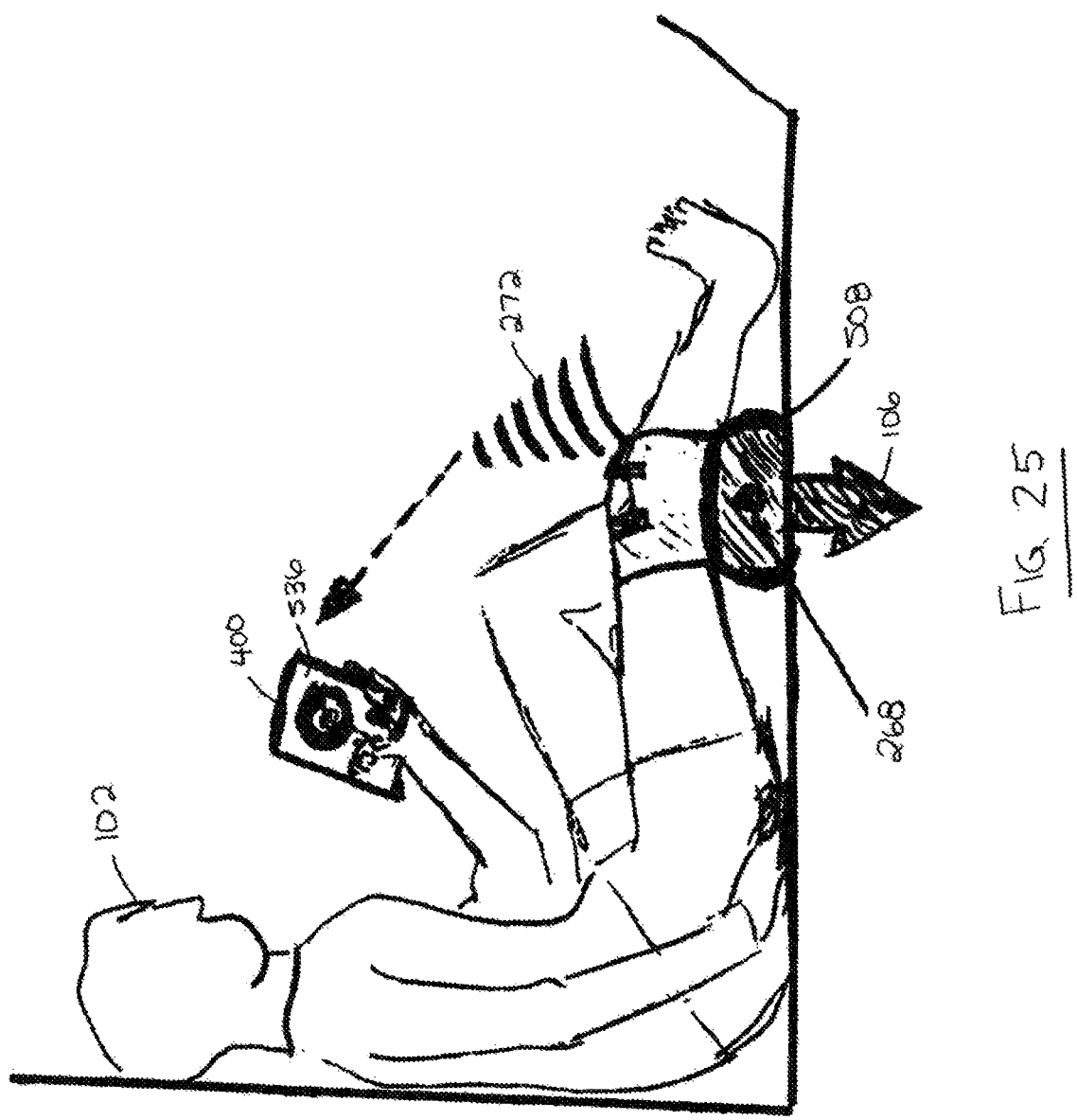
FIG. 25 is a side view of a user performing a one repetition maximum with a rehabilitation system in accordance with an embodiment.

Reference is now made to FIGS. 24, 25, and 29. At 712, the user is prompted to perform a one-repetition maximum (i.e. to perform a single repetition of the exercise to their maximum exertion). As mentioned above, the prompt may display each time a user starts a new workout, after a predetermined period from a previous workout, or before each exercise in a workout for example. FIG. 25 shows an example of a user performing an exercise with an exercise device 508, while transmitter 268 sends resistance member information 272 (including sensory data indicative of resistance met) to electronic device 400. During a one-repetition maximum, a user 102 may exert as much force 106 as they are capable of exerting in a single repetition. Transmitter 268 may send sensory data to electronic device 400 indicative of the exerted force, which may optionally be presented on display 536.

Still referring to FIGS. 24, 25, and 29, display 536 may visually present the resistance met (e.g. in units of force as shown, stress, strain, elongation, other real or fictitious units, or unitless) in any form, such as a dial gauge 576, numeric indication 580, or graph 584. After the one repetition maximum is completed (e.g. the user ceases to apply force 106), electronic device 400 may record the one repetition maximum resistance (i.e. in memory 416, FIG. 15). The recorded one repetition maximum resistance is determined based on the sensory data associated with the user's performance of the one repetition maximum. For example, the recorded one repetition maximum resistance may be a maximum attained resistance value 588, a mean time-weight resistance value 592, or a maximum sustained resistance value 596 (e.g. sustained for over a minimum predetermined period).

Figure 26:
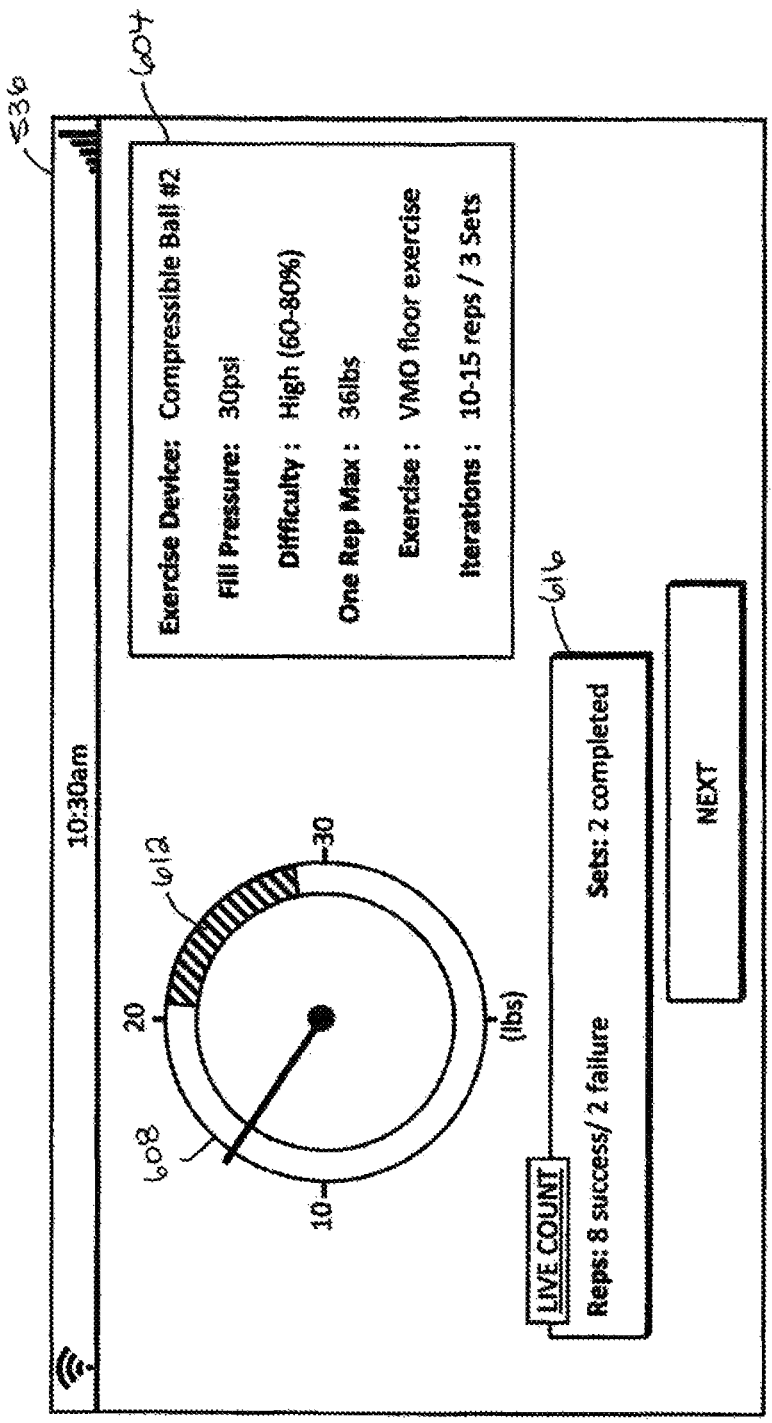
FIG. 26 is a schematic illustration of a display of a user electronic device, presenting contemporaneous exercise information, in accordance with an embodiment.

Referring to FIGS. 25-26 and 29, at 724 the user may perform the exercise according to the recorded one repetition maximum resistance and the set threshold percentage (s). As shown, display 536 that may present (in any suitable form) to the user, during the exercise, one or more (or all) of: exercise information 604, contemporaneous resistance 608, target resistance (or resistance range) 612 to register as a repetition or start an isometric-interval timer, and a contemporaneous iteration count 616. The display of resistance 608 may permit the user to control their exertion during the exercise so that they achieve resistances that satisfy the set predetermined threshold percentage (or percentage range) of the recorded one rep maximum resistance for each repetition or isometric-interval.

In some embodiments, in response to the user failing to satisfy the threshold percentage (or percentage range), electronic device 400 may record a failed repetition or stop an isometric-interval timer. For example, a failed repetition may be determined when the resistance increases from a minimum resistance value (e.g. close to or equal to zero resistance) and then returns to below the minimum resistance value without satisfying the threshold percentage (or percentage range). Similarly, a failed isometric-interval may be determined when the resistance increases from a minimum resistance value (e.g. close to or equal to zero resistance) and then returns to below the minimum resistance value without satisfying the threshold percentage (or percentage range) for at least the prescribed interval period (e.g. 10 seconds).

Figure 27:
FIG. 27 is a schematic illustration of a display of a user electronic device, presenting an exercise summary report, in accordance with an embodiment.

Reference is now made to FIGS. 27 and 29. At 728, electronic device 400 may generate an exercise report. As shown, display 536 may be presented to the user following the completion of the exercise. Display 536 may include one or more (or all) of: a summary of iteration counts 620, self-assessment fields 624, a performance score 628, and an option 640 to progress to a higher difficulty (or higher threshold percentage or percentage range).

The summary of iteration counts 620 may indicate the number of successful iterations (e.g. reps, intervals, and/or sets). As shown, summary 620 may also indicate the number of failed iterations.

Self-assessment fields 624 may allow a user to input self-assessed information, such as a pain rating 632 experienced during the exercise, and a performance difficulty 636 from the user's perspective.

The performance score 628 may be determined based at least in part on the registered successful and failed repetitions. For example, a higher performance score 628 may be determined if one or more of: (i) the number of successful iterations satisfies the prescribed iterations (e.g. reps, intervals, sets), and (ii) there are few or no failed iterations (e.g. failed repetitions or prematurely stopped isometric-interval timers). A lower performance score 628 may be determined if one or more of: (i) the number of successful iterations does not satisfy the prescribed iterations, and (ii) there are many failed iterations. The performance score 628 may be positively correlated to number of successful iterations, and negatively correlated to number of failed iterations. In some embodiments, the determination of performance score 628 may also consider the user's self-assessed information. For example, a lower pain rating 632 and a lower performance difficulty rating 636 may contribute to a higher performance score 628 and vice versa.

At 732 and 736, progress option field 640 may provide the user with an option to increase the threshold resistance percentage (or percentage range) if the performance score 628 exceeds a predetermined threshold performance score. As an example, the predetermined threshold performance score may be attainable when the user one or more of: satisfies the prescribed iterations, has few or no failed iterations, reports little or no pain, and reports low difficulty. Attainment of the threshold performance score may represent that the user's condition (e.g. strength, progress in their rehabilitation goals, etc.) has improved, and the user can safely increase their exertion level (relative to their one rep maximum). All else being equal, performance of exercises at a higher threshold resistance percentage (or percentage range) may accelerate the gains (e.g. in strength) achieved from performing the exercises.

Alternatively or in addition, electronic device 400 may determine at 732 and 736 (i.e. in accordance with the execution of computer readable instructions) to automatically increase or decrease the threshold resistance percentage (or percentage range) based on the performance score exceeding or falling below an upper or lower threshold performance score respectively. This may avoid burdening the user with deciding when to increase or decrease the threshold performance score, and instead rely on logic programmed into electronic device 400.

Figure 28:
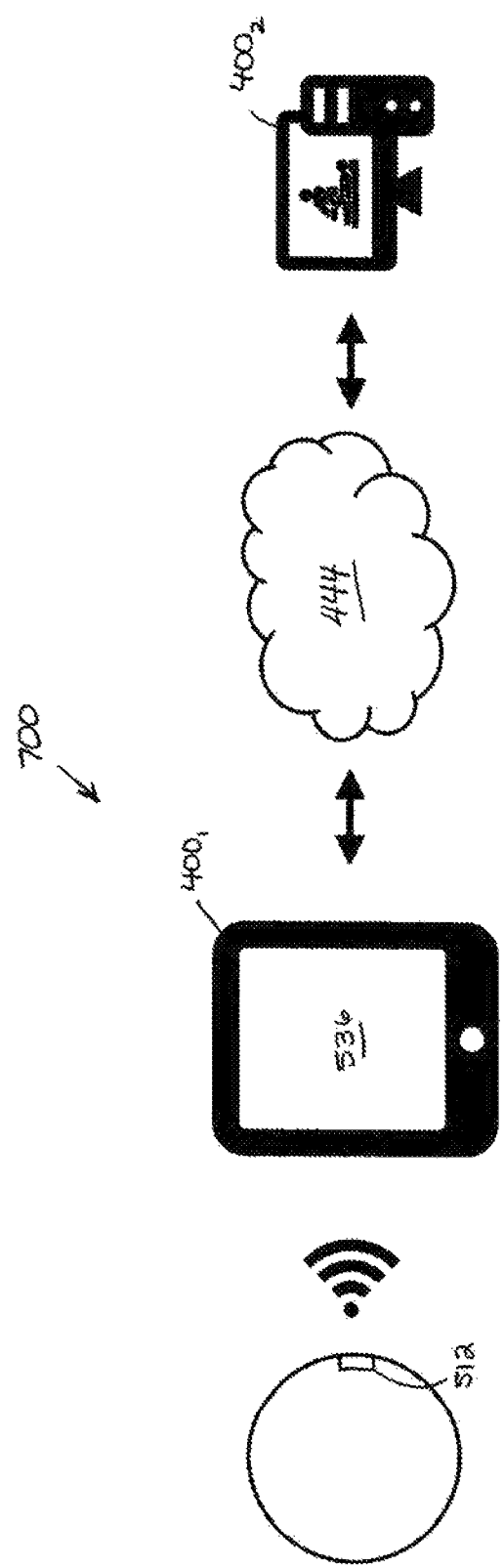
FIG. 28 is a schematic illustration of a rehabilitation system communicatively coupled to a remote physiotherapist device over a network, in accordance with an embodiment.

Referring to FIGS. 28 and 29, FIG. 28 shows a schematic illustration of a rehabilitation system 700 communicatively coupled to a remote physiotherapist device $400_2$ over a network 444. As shown, rehabilitation system 700 may include at least resistance sensor 512 and user device $400_1$.

In use, user device $400_1$ may receive from physiotherapist device $400_2$ over network 444 details of a physiotherapy regimen, including for example a threshold resistance percentage (or percentage range) for each of one or more exercises. In some embodiments, user device $400_1$ may send at 740 to physiotherapist device $400_2$ over network 444 exercise reports, including for example performance score 628 (FIG. 30), self assessed information 624 (FIG. 30), and/or iteration count summary 620 (FIG. 30). The physiotherapist may review the exercise report, make a professional assessment of if/how to change the user's physiotherapy regimen (e.g. change the exercises, iterations, and/or threshold percentages), and then at 744 send those changes to the user device $400_1$. Subsequently, the user will be directed to perform their exercise regimen by exercise device $400_1$ in accordance with the new parameters received from the physiotherapist device $400_2$.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

Items
1. A knee rehabilitation system comprising:
    a plurality of compressible resistance members,
        each compressible resistance member in the plurality of compressible resistance members having (i) a same size and shape as each other compressible resistance member in the plurality of compressible resistance members, and (ii) a compression resistance different from each other compressible resistance member in the plurality of compressible resistance members;
    a knee garment having a knee garment ventral portion and a knee garment dorsal portion; and
    a resistance member receptacle coupled to the knee garment dorsal portion, the resistance member receptacle sized to carry each compressible resistance member in the plurality of compressible resistance members, one at a time.

2. The knee rehabilitation system of any preceding item, wherein the shape of each compressible resistance member in the plurality of compressible resistance members is ellipsoidal.
3. The knee rehabilitation system of any preceding item, wherein the shape of each compressible resistance member in the plurality of compressible resistance members is substantially spherical.
4. The knee rehabilitation system of any preceding item, wherein the shape of each compressible resistance member in the plurality of compressible resistance members is non-ellipsoidal.
5. The knee rehabilitation system of any preceding item, wherein:
    each compressible resistance member in the plurality of compressible resistance members has a lateral side, a medial side, and a lateral width of between 5 and 9 inches measured along a frontal axis from the lateral side to the medial side.
6. The knee rehabilitation system of any preceding item when dependent on claim 3, wherein the lateral width defines a diameter of each compressible resistance member in the plurality of compressible resistance.
7. The knee rehabilitation system of any preceding item, wherein each compressible resistance member in the plurality of compressible resistance members is one of inflated and user-inflatable.
8. The knee rehabilitation system of any preceding item, wherein the size and the shape of each compressible resistance member in the plurality of compressible resistance members is an inflated size and an inflated shape.
9. The knee rehabilitation system of any preceding item, wherein each compressible resistance member in the plurality of compressible resistance members has a wall thickness different from each other compressible resistance member in the plurality of compressible resistance members.
Item 10. The knee rehabilitation system of any preceding item, wherein each compressible resistance member in the plurality of compressible resistance members has a visual indicium representative of the compression resistance of that compressible resistance member.
Item 11. The knee rehabilitation system of any preceding item, wherein:
    the resistance member receptacle is movable between an open position and a closed position, and
    in the open position, the resistance member receptacle defines an opening sized to receive one of the compressible resistance members in the plurality of compressible resistance members.
Item 12. The knee rehabilitation system of any preceding item, wherein the resistance member receptacle further comprises:
    a first shell portion attached to the knee garment dorsal portion; and
    a second shell portion movably connected to the first shell portion between the open position and the closed position.
Item 13. The knee rehabilitation system of any preceding item, wherein in the closed position, the resistance member receptacle has an inner cavity bounded by the first shell portion and the second shell portions.
Item 14. The knee rehabilitation system of any preceding item, wherein the inner cavity is sized to hold any one of the plurality of compressible resistance members, one at a time.
Item 15. The knee rehabilitation system of any preceding item, wherein at least one of the ventral shell portion and the dorsal shell portion is resiliently stretchable.

Item 16. The knee rehabilitation system of any preceding item, wherein when the resistance member receptacle is in the closed position, the resistance member receptacle has at least one access opening.

Item 17. The knee rehabilitation system of any preceding item, wherein:
  each compressible resistance member in the plurality of compressible resistance members has a gas port; and
  when each compressible resistance member in the plurality of compressible resistance members is received in the resistance member receptacle, the gas port is alignable with the access opening.

Item 18. The knee rehabilitation system of any preceding item wherein:
  each compressible resistance member in the plurality of compressible resistance members has an inner gas volume;
  the knee rehabilitation system further comprises a pressure gauge having a pressure gauge gas inlet and a pressure display; and
  when a compressible resistance member in the plurality of compressible resistance members is held in the resistance member receptacle, the pressure gauge gas inlet is positionable in fluid communication with the inner gas volume of that compressible resistance member, the pressure display providing an indication of a pressure of the inner gas volume of that compressible resistance member.

Item 19. The knee rehabilitation system of any preceding item, wherein the pressure gauge further comprises an inflation bulb.

Item 20. The knee rehabilitation system of any preceding item, further comprising:
  an extension hose, the extension hose including a proximal end fluidly connected to the pressure gauge gas inlet and a distal end fluidly connected to the inner gas volume.

Item 21. The knee rehabilitation system of any preceding item, wherein each compressible resistance member in the plurality of compressible resistance members comprises at least one of polyvinyl chloride (PVC) and rubber.

Item 22. The knee rehabilitation system of any preceding item, wherein each compressible resistance member in the plurality of compressible resistance members comprises an air release valve.

Item 23. A knee compression garment comprising:
  a resiliently stretchable body comprising a first leg portion having a distal opening, a second leg portion having a proximal opening, and a knee portion connecting the first leg portion to the second leg portion, wherein the knee portion has a knee ventral portion and a knee dorsal portion; and
  a compressible resistance member mount connected to the knee dorsal portion and extending dorsally of the knee dorsal portion.

Item 24. The knee compression garment of any preceding item, wherein the knee ventral portion includes a patellar opening.

Item 25. The knee compression garment of any preceding item or claim 24, wherein a patellar tracking support is connected to the knee ventral portion.

Item 26. The knee compression garment of any preceding item, wherein the patellar tracking support comprises a first support end rotatably coupled to a lateral side of the knee ventral portion, and a second support end removably coupled to a medial side of the knee ventral portion.

Item 27. The knee compression garment of any preceding item, wherein the patellar tracking support is C-shaped having a closed C-end at the first support end, and an open C-end at the second support end.

Item 28. The knee compression garment of any preceding item when dependent on claim 24, wherein the patellar tracking support surrounds at least a portion of the patellar opening.

Item 29. The knee compression garment of any preceding item, wherein the compressible resistance member mount is sized to receive a compressible resistance member.

Item 30. The knee compression garment of any preceding item, wherein:
  the compressible resistance member mount is movable between an open position and a closed position, and
  in the open position, the compressible resistance member mount defines an opening sized to receive the compressible resistance member.

Item 31. The knee compression garment of any preceding item, wherein the compressible resistance member mount further comprises:
  a first shell portion attached to the knee dorsal portion; and
  a second shell portion movably connected to the first shell portion between the open position and the closed position.

Item 32. The knee compression garment of any preceding item, wherein in the closed position, the compressible resistance member mount has an inner cavity bounded by the first shell portion and the second shell portion.

Item 33. The knee compression garment of any preceding item, wherein the inner cavity is sized to hold the compressible resistance member.

Item 34. The knee compression garment of any preceding item, wherein at least one of the first shell portion and the second shell portion is resiliently stretchable.

Item 35. The knee compression garment of any preceding item, wherein when compressible resistance member mount is in the closed position, the compressible resistance member mount has at least one access opening.

Item 36. A method of knee rehabilitation comprising:
  securing a resistance member receptacle to a dorsal side of a user's knee;
  receiving a compressible resistance member in the resistance member receptacle; and
  performing a knee exercise that compresses the compressible resistance member between the dorsal side of the user's knee and a stationary surface.

Item 37. The method of any preceding item, wherein said securing the resistance member receptacle to the dorsal side of the use's knee comprises outfitting the user with a knee compression garment having the resistance member receptacle extending dorsally from a dorsal side of the knee compression garment.

Item 38. An rehabilitation system comprising:
  a resistance sensor connectable to an exercise device;
  a memory storing computer readable instructions and a lower threshold resistance percentage; and
  one or more processors collectively communicatively coupled to the resistance sensor and the memory, and configured to execute the computer-readable instructions, the computer readable instructions when executed configuring the one or more processors to collectively:
    (i) receive sensory data from the resistance sensor indicative of a one repetition maximum resistance measured by the resistance sensor, and after (i), one or many iterations of:
- a) receive, from the resistance sensor, sensory data indicative of a resistance measured by the resistance sensor, and
- b) in response to determining that the resistance exceeds the lower threshold resistance percentage of the one repetition maximum resistance, either register a successful repetition or start an isometric-interval timer.

Item 39. The rehabilitation system of any preceding item, wherein the computer readable instructions when executed further configure the one or more processors to collectively:
receive the lower threshold resistance percentage from a remote physiotherapist device over a network.

Item 40. The rehabilitation system of any preceding item, wherein the computer readable instructions when executed further configure the one or more processors to collectively:
receive user input that selects the lower threshold resistance percentage.

Item 41. The rehabilitation system of any preceding item, wherein the computer readable instructions when executed further configure the one or more processors to collectively:
before (i), output signals for prompting a user to perform a one repetition maximum with the exercise device.

Item 42. The rehabilitation system of any preceding item, wherein the computer readable instructions when executed further configure the one or more processors to collectively:
before (i), in response to determining that a user has changed exercises, output signals for prompting a user to perform a one repetition maximum with the exercise device.

Item 43. The rehabilitation system of any preceding item, wherein the computer readable instructions when executed further configure the one or more processors to collectively:
receive user input identifying an exercise the user will perform with the exercise device.

Item 44. The rehabilitation system of any preceding item, wherein the exercise comprises:
a number of sets and a number of repetitions per set, or a duration of an isometric-interval, and a number of isometric-intervals.

Item 45. The rehabilitation system of any preceding item, wherein the computer readable instructions when executed further configure the one or more processors to collectively:
before (i), in response to determining that a predetermined period has elapsed since a previous workout, output signals for prompting a user to perform a one repetition maximum with the exercise device.

Item 46. The rehabilitation system of any preceding item, wherein the computer readable instructions when executed further configure the one or more processors to collectively:
receive input indicative of a start of a new workout.

Item 47. The rehabilitation system of any preceding item, wherein:
the memory stores an upper threshold resistance percentage; and
step (b) comprises in response to determining that the resistance exceeds the lower threshold resistance percentage of the one repetition maximum resistance and is less than the upper threshold resistance percentage of the one repetition maximum resistance, either register the successful repetition or start the isometric-interval timer.

Item 48. The rehabilitation system of any preceding item, wherein the computer readable instructions when executed configuring the one or more processors to collectively:
in response to determining that the resistance is less than the lower threshold resistance percentage of the one repetition maximum resistance, either register a failed repetition or stop an isometric-interval timer.

Item 49. The rehabilitation system of any preceding item, wherein the computer readable instructions when executed configuring the one or more processors to collectively:
in response to determining that the resistance is greater than the upper threshold resistance percentage of the one repetition maximum resistance, either register a failed repetition or stop an isometric-interval timer.

Item 50. The rehabilitation system of any preceding item, wherein:
the resistance sensor comprises a pressure sensor.

Item 51. The rehabilitation system of any preceding item, wherein:
the resistance sensor comprises a strain sensor.

Item 52. The rehabilitation system of any preceding item, wherein:
the resistance sensor comprises a force sensor.

Item 53. The rehabilitation system of any preceding item, wherein:
the rehabilitation system comprises the exercise device.

Item 54. The rehabilitation system of any preceding item, wherein:
the exercise device comprises a compressible resistance member.

Item 55. The rehabilitation system of any preceding item, wherein:
the exercise device comprises an elastically stretchable band.

Item 56. The rehabilitation system of any preceding item, wherein the computer readable instructions when executed configuring the one or more processors to collectively:
after the one or more iterations, determine a performance score based at least in part on the registered successful and failed repetitions, or started and stopped intervals, and
in response to determining that the performance score exceeds a predetermined threshold performance score, increasing the lower threshold resistance percentage.

Item 57. The rehabilitation system of any preceding item, wherein the computer readable instructions when executed configuring the one or more processors to collectively:
after the one or more iterations, determine a performance score based at least in part on the registered successful and failed repetitions, or started and stopped intervals, and
in response to determining that the performance score exceeds a predetermined threshold, prompt a user with an option to increase the lower threshold resistance percentage.

Item 58. A rehabilitation method, the method comprising:
receiving, by one or more processors collectively, from a resistance sensor connected to an exercise device, sensory data indicative of a one repetition maximum resistance measured by the resistance sensor; and
after (i), one or more iterations of:
- a) receiving, from the resistance sensor, sensory data indicative of a resistance measured by the resistance sensor, and
- b) in response to determining that the resistance exceeds a lower threshold resistance percentage of the one repetition maximum resistance, either registering a successful repetition or starting an isometric-interval timer.

Item 59. The method of any preceding item, further comprising:
receiving the lower threshold resistance percentage from a remote physiotherapist device over a network.

Item 60. The method of any preceding item, further comprising:
receiving user input that selects the lower threshold resistance percentage.

Item 61. The method of any preceding item, further comprising:
before (i), outputting signals for prompting a user to perform a one repetition maximum with the exercise device.

Item 62. The method of any preceding item, further comprising:
before (i), in response to determining that a user has changed exercises, outputting signals for prompting a user to perform a one repetition maximum with the exercise device.

Item 63. The method of any preceding item, further comprising:
receiving user input identifying an exercise the user will perform with the exercise device.

Item 64. The method of any preceding item, wherein the exercise comprises:
a number of sets and a number of repetitions per set, or
a duration of an isometric-interval, and a number of isometric-intervals per set.

Item 65. The method of any preceding item, further comprising:
before (i), in response to determining that a predetermined period has elapsed since a previous workout, outputting signals for prompting a user to perform a one repetition maximum with the exercise device.

Item 66. The method of any preceding item, further comprising:
receiving input indicative of a start of a new workout.

Item 67. The method of any preceding item, wherein:
step (b) comprises in response to determining that the resistance exceeds the lower threshold resistance percentage of the one repetition maximum resistance and is less than an upper threshold resistance percentage of the one repetition maximum resistance, either registering the successful repetition or starting the isometric-interval timer.

Item 68. The method of any preceding item, further comprising:
in response to determining that the resistance is less than the lower threshold resistance percentage of the one repetition maximum resistance, either registering a failed repetition or stopping an isometric-interval timer.

Item 69. The method of any preceding item, further comprising:
in response to determining that the resistance is greater than the upper threshold resistance percentage of the one repetition maximum resistance, either registering a failed repetition or stopping an isometric-interval timer.

Item 70. The method of any preceding item, wherein:
the resistance sensor comprises a pressure sensor.

Item 71. The method of any preceding item, wherein:
the resistance sensor comprises a strain sensor.

Item 72. The method of any preceding item, wherein:
the resistance sensor comprises a force sensor.

Item 73. The method of any preceding item, wherein:
the exercise system comprises the exercise device.

Item 74. The method of any preceding item, wherein:
the exercise device comprises a compressible resistance member.

Item 75. The method of any preceding item, wherein:
the exercise device comprises an stretchable band.

Item 76. The method of any preceding item, further comprising:
after the one or more iterations, determining a performance score based at least in part on the registered successful and failed repetitions, or started and stopped intervals, and
in response to a comparison of the performance score to a predetermined threshold performance score, increasing the lower threshold resistance percentage.

Item 77. The method of any preceding item, wherein the computer readable instructions when executed configuring the one or more processors to collectively:
after the one or more iterations, determining a performance score based at least in part on the registered successful and failed repetitions, or started and stopped intervals, and
in response to a comparison of the performance score to a predetermined threshold performance score, prompting a user with an option to increase the lower threshold resistance percentage.

The invention claimed is:

1. A rehabilitation system comprising:
a resistance sensor connectable to an exercise device;
a memory storing computer readable instructions and a lower threshold resistance percentage; and
one or more processors collectively communicatively coupled to the resistance sensor and the memory, and configured to execute the computer-readable instructions, the computer readable instructions when executed configuring the one or more processors to collectively:
(i) receive sensory data from the resistance sensor indicative of a one repetition maximum resistance measured by the resistance sensor,
after (i), one or many iterations of:
a) receive, from the resistance sensor, sensory data indicative of a resistance measured by the resistance sensor, and
b) in response to determining that the resistance exceeds the lower threshold resistance percentage of the one repetition maximum resistance, either register a successful repetition or start an isometric-interval timer; and
before (i), in response to a change of exercise, output signals for prompting a user to perform a one repetition maximum with the exercise device.

2. The rehabilitation system of claim 1, wherein the computer readable instructions when executed further configure the one or more processors to collectively:
receive the lower threshold resistance percentage from a remote physiotherapist device over a network.

3. The rehabilitation system of claim 1, wherein the computer readable instructions when executed further configure the one or more processors to collectively:
receive user input that selects the lower threshold resistance percentage.

4. The rehabilitation system of claim 1, wherein:
the memory stores an upper threshold resistance percentage; and
step (b) comprises in response to determining that the resistance exceeds the lower threshold resistance percentage of the one repetition maximum resistance and is less than the upper threshold resistance percentage of the one repetition maximum resistance, either register the successful repetition or start the isometric-interval timer.

5. The rehabilitation system of claim 4, wherein the computer readable instructions when executed configuring the one or more processors to collectively:
in response to determining that the resistance is greater than the upper threshold resistance percentage of the one repetition maximum resistance, either register a failed repetition or stop an isometric-interval timer.

6. The rehabilitation system of claim 1, wherein the computer readable instructions when executed configuring the one or more processors to collectively:
in response to determining that the resistance is less than the lower threshold resistance percentage of the one repetition maximum resistance, either register a failed repetition or stop an isometric-interval timer.

7. The rehabilitation system of claim 6, wherein the computer readable instructions when executed configuring the one or more processors to collectively:
after the one or more iterations, determine a performance score based at least in part on the registered successful and failed repetitions, or started and stopped intervals, and
in response to determining that the performance score exceeds a predetermined threshold performance score, increasing the lower threshold resistance percentage.

8. The rehabilitation system of claim 6, wherein the computer readable instructions when executed configuring the one or more processors to collectively:
after the one or more iterations, determine a performance score based at least in part on the registered successful and failed repetitions, or started and stopped intervals, and
in response to determining that the performance score exceeds a predetermined threshold, prompt a user with an option to increase the lower threshold resistance percentage.

9. A rehabilitation method, the method comprising:
receiving, by one or more processors collectively, from a resistance sensor connected to an exercise device, sensory data indicative of a one repetition maximum resistance measured by the resistance sensor;
after (i), one or more iterations of:
a) receiving, from the resistance sensor, sensory data indicative of a resistance measured by the resistance sensor, and
b) in response to determining that the resistance exceeds a lower threshold resistance percentage of the one repetition maximum resistance, either registering a successful repetition or starting an isometric-interval timer; and
before (i), in response to a change of exercise, outputting signals for prompting a user to perform a one repetition maximum with the exercise device.

10. The method of claim 9, further comprising:
receiving the lower threshold resistance percentage from a remote physiotherapist device over a network.

11. The method of claim 9, further comprising:
receiving user input that selects the lower threshold resistance percentage.

12. The method of claim 9, wherein:
step (b) comprises in response to determining that the resistance exceeds the lower threshold resistance percentage of the one repetition maximum resistance and is less than an upper threshold resistance percentage of the one repetition maximum resistance, either registering the successful repetition or starting the isometric-interval timer.

13. The method of claim 12, further comprising:
in response to determining that the resistance is greater than the upper threshold resistance percentage of the one repetition maximum resistance, either registering a failed repetition or stopping an isometric-interval timer.

14. The method of claim 9, further comprising:
in response to determining that the resistance is less than the lower threshold resistance percentage of the one repetition maximum resistance, either registering a failed repetition or stopping an isometric-interval timer.

15. The method of claim 14, further comprising:
after the one or more iterations, determining a performance score based at least in part on the registered successful and failed repetitions, or started and stopped intervals, and
in response to a comparison of the performance score to a predetermined threshold performance score, increasing the lower threshold resistance percentage.

16. The method of claim 14, wherein the computer readable instructions when executed configuring the one or more processors to collectively:
after the one or more iterations, determining a performance score based at least in part on the registered successful and failed repetitions, or started and stopped intervals, and
in response to a comparison of the performance score to a predetermined threshold performance score, prompting a user with an option to increase the lower threshold resistance percentage.

17. A non-transitory computer-readable medium comprising instructions executable by one or more processors, wherein the instructions when executed configure the one or more processors to collectively:
receive sensory data, from a resistance sensor connected to an exercise device, indicative of a one repetition maximum resistance measured by the resistance sensor;
after (i), one or many iterations of:
a) receive, from the resistance sensor, sensory data indicative of a resistance measured by the resistance sensor, and
b) in response to determining that the resistance exceeds the lower threshold resistance percentage of the one repetition maximum resistance, either register a successful repetition or start an isometric-interval timer; and
before (i), in response to a change of exercise, output signals for prompting a user to perform a one repetition maximum with the exercise device.

* * * * *